(12) United States Patent
Miller et al.

(10) Patent No.: US 8,685,002 B2
(45) Date of Patent: Apr. 1, 2014

(54) DATA STORAGE FOR AN INFUSION PUMP SYSTEM

(75) Inventors: Steve Miller, Palo Alto, CA (US); Mark C. Estes, Malibu, CA (US); Ken Mochel, San Jose, CA (US); David Rich, Morgan Hill, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 58 days.

(21) Appl. No.: 13/468,077

(22) Filed: May 10, 2012

(65) Prior Publication Data

US 2012/0220936 A1    Aug. 30, 2012

Related U.S. Application Data

(62) Division of application No. 13/095,632, filed on Apr. 27, 2011, now Pat. No. 8,211,093, which is a division of application No. 11/851,986, filed on Sep. 7, 2007, now Pat. No. 7,935,105.

(51) Int. Cl.
*A61K 9/22*    (2006.01)

(52) U.S. Cl.
USPC .......................................................... 604/890.1

(58) Field of Classification Search
USPC ................ 604/65, 66, 67, 131, 151, 890.1
See application file for complete search history.

(56) References Cited

U.S. PATENT DOCUMENTS

| | | |
|---|---|---|
| 2,605,765 A | 8/1952 | Kollsman |
| 3,886,938 A | 6/1975 | Szabo et al. |
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,045,064 A | 9/1991 | Idriss |

(Continued)

FOREIGN PATENT DOCUMENTS

| | | |
|---|---|---|
| CA | 2543545 | 5/2005 |
| DE | 196 27 619 | 1/1998 |

(Continued)

OTHER PUBLICATIONS

Medtronic News Release, "Medtronic Receives FDA Approval for World's First Insulin Pump with Real-time Continuous Glucose Monitoring," Apr. 13, 2006, 3 pages.

(Continued)

*Primary Examiner* — Aarti B Berdichevsky

(74) *Attorney, Agent, or Firm* — Fish & Richardson P.C.

(57) ABSTRACT

A pump system can include a pump device and a controller device removably attachable to the pump device. The controller device can be reusable, and one or more pump devices can be disconnected and reconnected to the controller device. As such, some pump usage data can be conveniently stored in the pump device itself. In such circumstances, the controller device can receive data related to the pump's history or other usage when the pump device is attached to the controller.

21 Claims, 18 Drawing Sheets

(56) References Cited

U.S. PATENT DOCUMENTS

| | | |
|---|---|---|
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,404,796 B2 | 7/2008 | Ginsberg |
| 7,935,105 B2 * | 5/2011 | Miller et al. ............ 604/890.1 |
| 8,105,279 B2 * | 1/2012 | Mernoe et al. ............ 604/131 |
| 8,287,514 B2 * | 10/2012 | Miller et al. ............ 604/500 |

(56) References Cited

U.S. PATENT DOCUMENTS

| | | |
|---|---|---|
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0169439 A1 | 11/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0167035 A1 | 9/2003 | Flaherty et al. |
| 2003/0199825 A1 | 10/2003 | Flaherty |
| 2003/0216683 A1 | 11/2003 | Shekalim |
| 2004/0008117 A1* | 1/2004 | Kawakami ............... 340/636.1 |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0079765 A1 | 4/2006 | Neer et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1* | 3/2007 | Estes et al. ............... 604/151 |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0179444 A1* | 8/2007 | Causey et al. ............... 604/131 |
| 2008/0208627 A1 | 8/2008 | Skyggebjerg |
| 2011/0112504 A1* | 5/2011 | Causey et al. ............... 604/500 |
| 2012/0022496 A1* | 1/2012 | Causey et al. ............... 604/500 |
| 2012/0123384 A1* | 5/2012 | Mernoe et al. ............... 604/500 |
| 2012/0130312 A1* | 5/2012 | Mernoe et al. ............... 604/152 |
| 2012/0302991 A1* | 11/2012 | Blomquist et al. ............ 604/504 |
| 2013/0012917 A1* | 1/2013 | Miller et al. ............... 604/500 |

FOREIGN PATENT DOCUMENTS

| | | |
|---|---|---|
| DE | 102 36 669 | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 384 490 | 1/2004 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.
Patent Abstracts of Japan, vol. 1999, No. 4, and JP 11 010036, Apr. 30, 1999 and Jan. 19, 1999, Toray Ind. Inc.
Invitation to Pay Fees, PCT/US2008/070148, mailed Feb. 16, 2009, 10 pages.
International Search Report & Written Opinion PCT/US2008/070148, mailed Apr. 29, 2009, 19 pages.
International Preliminary Report on Patentability for Application PCT/US2008/070148, dated Mar. 18, 2010, 12 pages.

* cited by examiner

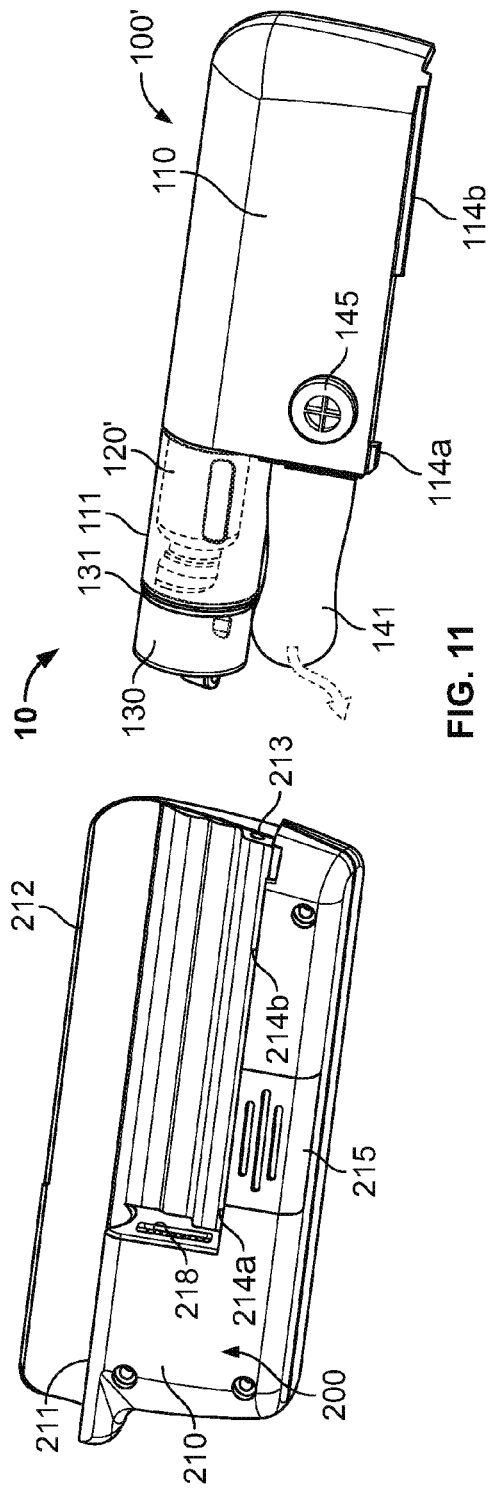
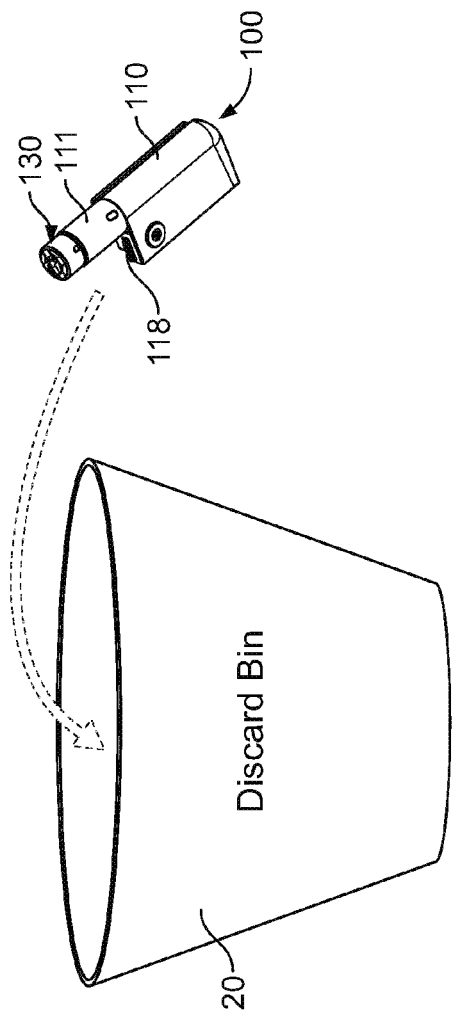
FIG. 11
FIG. 12

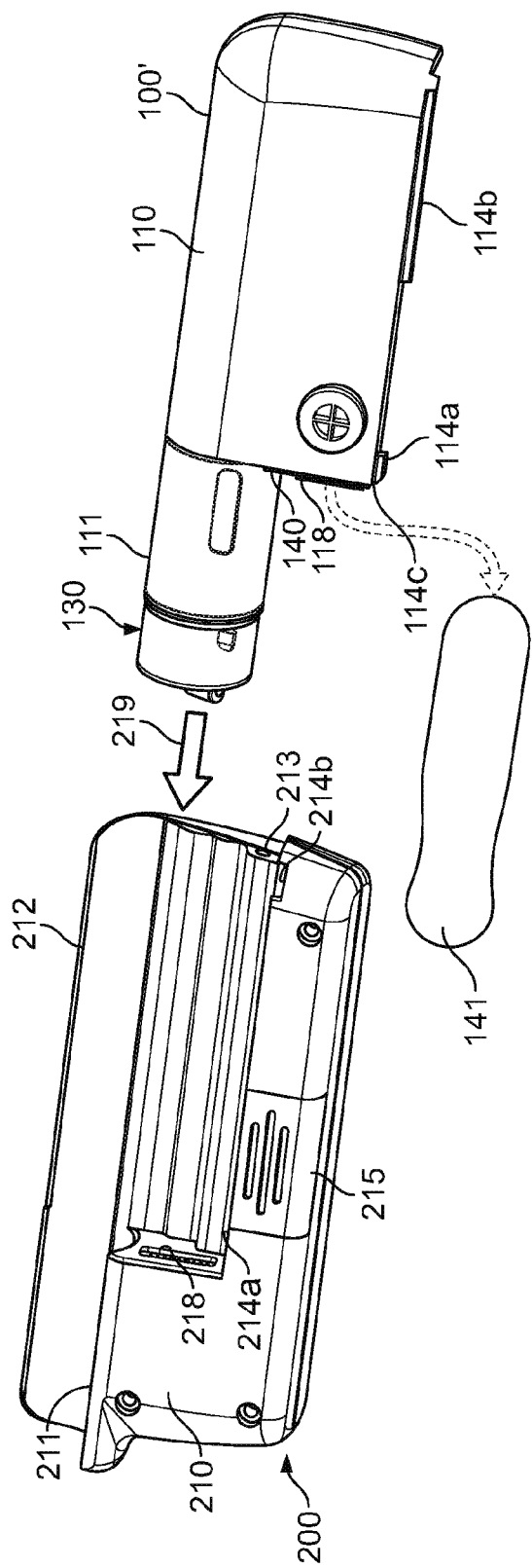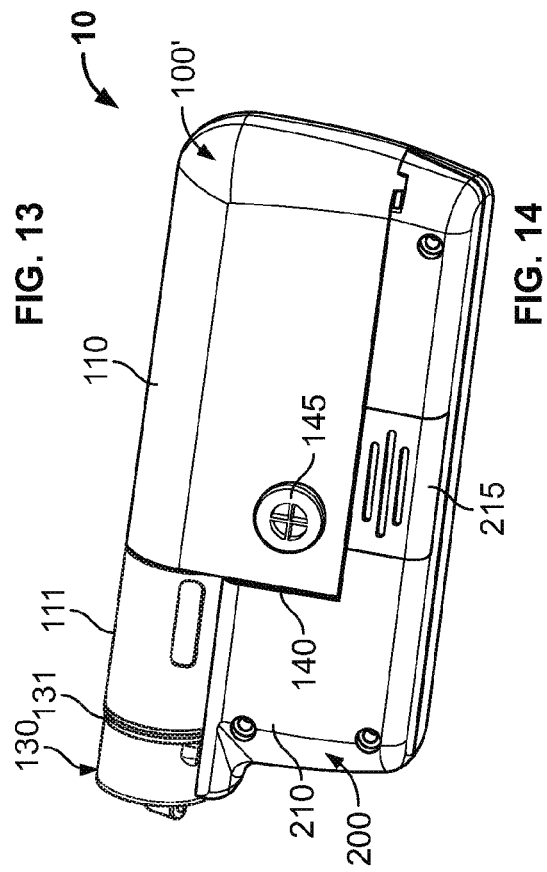
FIG. 13
FIG. 14

318

| Event Log | | |
|---|---|---|
| Date + Time | Medicine Dosage (In Clicks) | Food Consumption (User Input in Grams) of Carbohydrates |
| 2007.08.31 22.15 | 1 Units | — |
| 2007.08.31 23.14 | 0.5 Units | 10g |
| 2007.08.31 23.55 | — | 5g |
| 2007.09.01 02.13 | 0.5 Units | — |
| 2007.09.01 08.19 | 0.5 Units | 15g |
| 2007.09.01 10.45 | 0.5 Units | — |
| 2007.09.01 12.33 | 1.5 Units | 25g |
| 2007.09.01 02.20 | — | 10g |

FIG. 19

| Unique User Profile | |
|---|---|
| Identifier | John Q Smith 123-04-5678 |
| Medicine Types | Insulin Symlin® |
| Insulin Sensitivity | 0.6 |
| Carbohydrate Ratio | 1.3 |
| Height | 5' 10" |
| Weight | 185 lb |
| Gender | M |
| Basal Insulin Rates | 2.3 |
| Blood Glucose to Activity Ratio | 0.7 |

FIG. 20

DATA STORAGE FOR AN INFUSION PUMP SYSTEM

CROSS-REFERENCE TO RELATED APPLICATION(S)

This is a division of U.S. application Ser. No. 13/095,632 filed on Apr. 27, 2011, which is a division of U.S. application Ser. No. 11/851,986 filed on Sep. 7, 2007, the contents of these prior applications being incorporated herein by reference.

TECHNICAL FIELD

This document relates to storing information related to usage of a pump device, in one or more memory devices of an infusion pump device.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

SUMMARY

A pump system can include a pump device and a controller device removably attachable to the pump device. The controller device can be reusable, and one or more pump devices can be disconnected and reconnected to the controller device. As such, some pump usage data can be conveniently stored in the pump device itself. In such circumstances, the controller device can receive data related to the pump's history or other usage when the pump device is attached to the controller.

In particular embodiments, a wearable infusion pump system can include a pump device and a controller device that is removably attachable to the pump device. The pump device may define a space to receive a medicine source and can include a drive system to dispense medicine from the pump device when the medicine source is received in the space. The pump device can include a memory device that stores an event log of pump system operations. The controller device can activate the drive system to dispense the medicine source and can record data to the event log on the memory device when the controller device is removably attached to the pump device.

In some embodiments, a wearable infusion pump system can include a pump device and a controller device that is removably attachable to the pump device. The pump device may define a space to receive a medicine source and can include a drive system to dispense medicine from the pump device when the medicine source is received in the space. The pump device can include a memory device storing an energy requirement profile to perform a medicine dispensing operation. The energy requirement profile can be defined by the drive system of the pump device. The controller device can receive the energy requirement profile from the memory device and initiate a medicine dispensing operation by supplying a pattern of voltage pulses from the energy storage source to the drive system. The pattern of voltage pulses may be correlated to the energy requirement profile of the drive system.

In other embodiments, a wearable infusion pump system can include a pump device and a controller device that is removably attachable to the pump device. The pump device may define a space to receive a medicine source and can include a drive system to dispense medicine from the pump device when the medicine source is received in the space. The pump device may also include a battery. The pump device can including a memory device that stores data indicative of a charge level of the battery. The controller device can activate the drive system to dispense the medicine source and can receive the data indicative of the charge level of the battery.

In particular embodiments, a method of storing information regarding a pump device may include initiating one or more pump system operations of a pump device removably attached to a controller device. The pump device may include a medicine and a drive system to dispense the medicine from the pump device. Also, the pump device can include a memory device. The controller device can communicate data to the memory device when the controller device is removably attached to the pump device. The method may further include communicating event log data from the controller device to memory device of the pump device. The event log data may be indicative of the pump system operations.

In particular embodiments, a wearable infusion pump system may include a disposable and non-reusable pump device defining a space to receive a medicine cartridge. The pump device can include a drive system to dispense medicine from the pump device when the medicine cartridge is received in the space. The pump device can include a memory device storing an event log of pump system operations on the memory device. The system can also include a reusable controller device removably attachable to the pump device. The controller device can include a user interface. The controller device can activate the drive system to dispense the medicine source and record data to the event log on the memory device when the controller device is removably attached to the pump device. The controller device can include control circuitry communicating control signals to the drive system to dispense the medicine.

Some or all of the embodiments described herein may provide one or more of the following advantages. First, some embodiments of an infusion pump system may include a configuration that records an event log on a memory device in the pump device. This configuration may permit a physician or counselor to help check compliance with recommended dosages or diet protocols by accessing the pump device. Moreover, the recorded data of a user's medical dosages and eating habits can enhance the ability of the user or a medical practitioner to perform retrospective analysis and correction of the medicine delivery profile.

Second, some embodiments of the infusion pump system can include a memory device in a pump device that stores an energy requirement profile for the drive system of the pump device. By storing an energy requirement profile for the drive system in the memory device in the pump device, a controller can quickly determine the appropriate energy delivery profile for completing a medicine dispensing operation. Moreover, the controller can detect situation where the delivered energy profile is insufficient, correct the delivered energy profile, and record the corrected energy requirement profile as a new energy requirement profile on the memory device in the pump device. If the pump device is disconnected from the controller and reattached to the same or even a different controller, the controller can use the corrected energy requirement profile without having to re-correct the energy requirement profile.

Third, some embodiments of the infusion pump system may include a memory device in a pump device that stores data indicative of the battery life of a battery in the pump device. For example, the memory device can store an indication of whether the battery life of the battery in the pump device is in a depleted or non-depleted state. Once a controller has determined that the pump battery is in a depleted state, the controller can write data to the memory device in the pump device to indicate that the pump battery is in a depleted state. This can prevent the controller from attempting to use a depleted pump battery after an initial determination, even if the pump device has been disconnected from the controller and either reconnected to the same controller or connected to a new controller. In some embodiments, the controller can estimate an amount of battery life remaining and store this data on the memory device.

Fourth, some embodiments of the controller device are configured to removably attach to the pump device in a manner that provides a reliable electrical connection therebetween. Such an electrical connection may permit communication from the controller device to the drive system of the pump device.

Fifth, some embodiments of the pump device may be attached to the controller device so that a user can readily monitor infusion pump operation by simply viewing the user interface connected to the pump device. In these circumstances, the user may activate and control the pump device without the requirement of locating and operating a separate monitoring module.

Sixth, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments set forth in the accompanying drawings and the description below. Other features, objects, and advantages will be apparent from the description and drawings, and from the claims.

DESCRIPTION OF DRAWINGS

FIGS. 9, 10, and 11 are perspective views of a pump device being detached from a controller device, in accordance with some embodiments.

FIGS. 12-13 are perspective views of the pump device of FIGS. 11-12 being discarded and the controller device of FIGS. 11-12 being reused with a new pump device.

FIGS. 14-15 are perspective views of the new pump device of FIG. 12 being attached to the controller device of FIG. 12.

FIG. 15 is an exploded perspective view of a controller device for an infusion pump system, in accordance with some embodiments.

FIG. 19 is an example of an event log that can be stored in a memory device in a pump device.

FIG. 20 is an example of user profile data that can be stored in a memory device in a pump device.

Like reference symbols in the various drawings indicate like elements.

DETAILED DESCRIPTION OF ILLUSTRATIVE EMBODIMENTS

Figure 1:
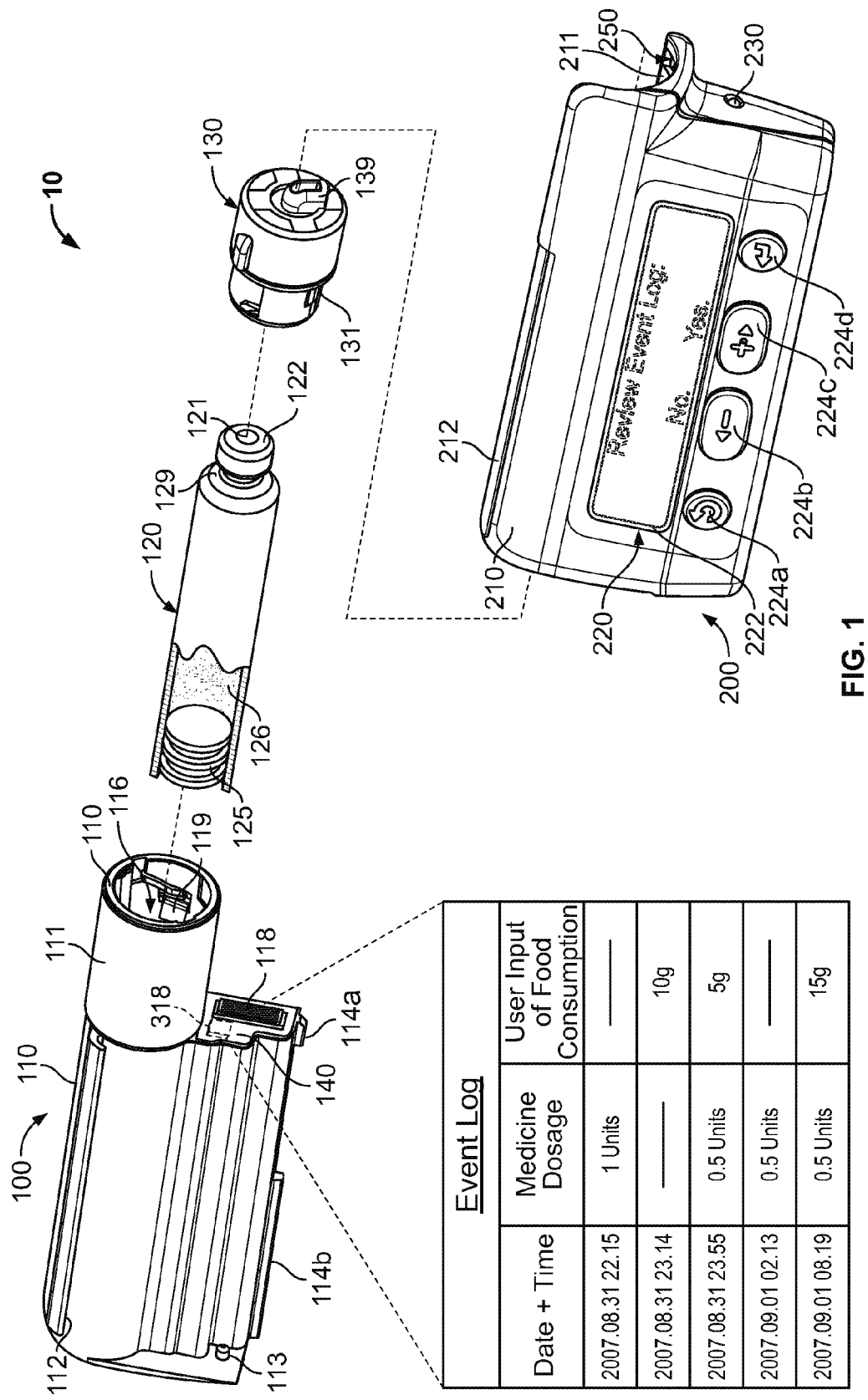
FIG. 1 is a perspective view of an infusion pump system in accordance with some embodiments.
Figure 2:
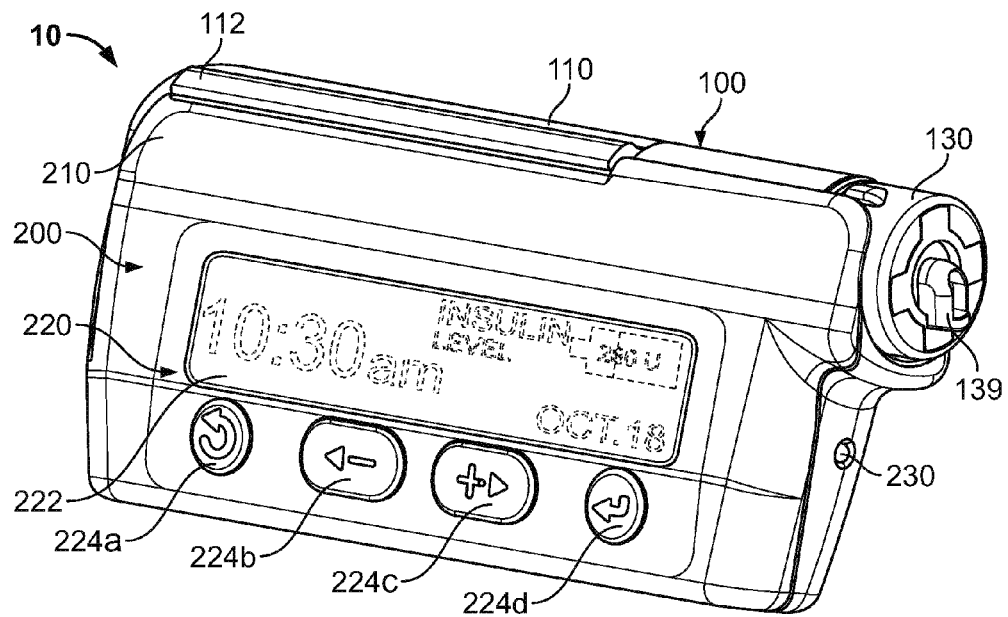
FIG. 2 is a perspective view of the infusion pump system of FIG. 1 in an assembled state.
Figure 3:
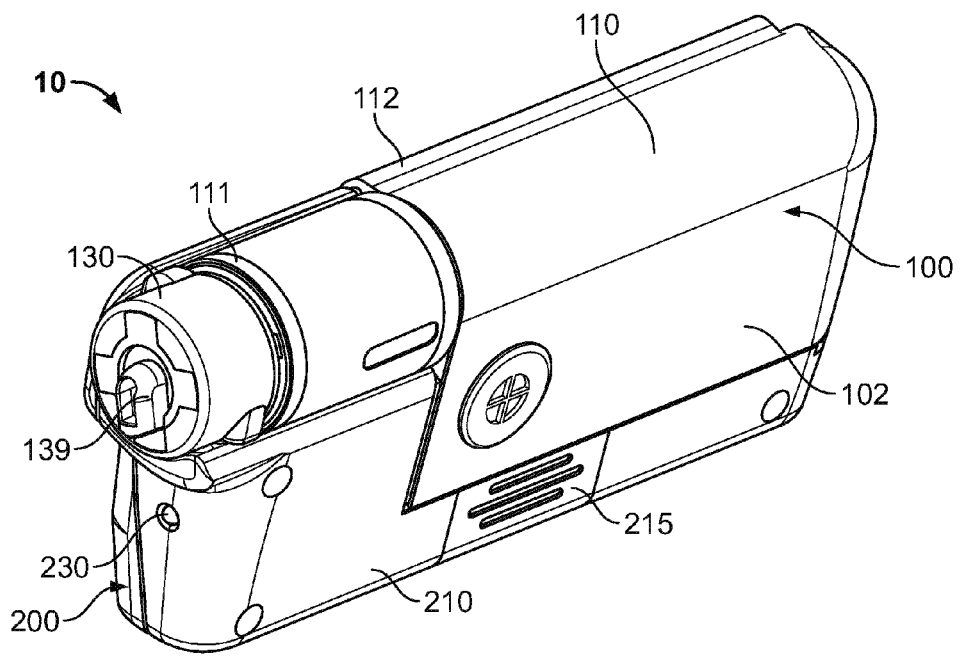
FIG. 3 is another perspective view of the infusion pump system of FIG. 2.

Referring to FIGS. 1-3, an infusion pump system 10 can include a pump device 100 and a controller device 200 that communicates with the pump device 100. The pump device 100 can include a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (described in more detail below) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 9-14, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

In some embodiments, a user may use a controller device 200 to dispense more than one drug in sequence from different pump devices 100, which may mean that a user swaps the pump devices 100 before the fluid cartridge 120 is empty. For example, a diabetic may use the controller device 200 and a series of pump devices 100 for dispensation of more than one type of insulin. Accordingly, in these embodiments, a user may detach and reattach a pump device 100 from the controller device 200 before discarding the pump device 100 when the fluid cartridge 120 is exhausted. In these embodiments, the detachment and reattachment of the pump device 100 from the controller device 200 can be accommodated.

For example, a memory device 318 included in the pump device 100 can store data related to the pump device 100. The memory device 318 can be configured to store pump-related data such as: a unique serial number designated for the pump device 100; a manufacturer identifier code; a lot number code; a manufacturing date stamp; a model number; compatibility codes used to ensure that the pump device 100, the controller device 200, and the fluid cartridge 120 can work together; a energy requirement profile for the drive system of the pump device; an event log including time and date stamped records of pump activations, user input, and/or sensor input (refer to FIGS. 1 and 19); data regarding the pump battery life (e.g., the power remaining in the first power source 345); a drive cycle counter; an estimation of pump motor run time; and an estimation of the medicine remaining in the fluid cartridge 120. The data stored on the memory device 318 can be received by the controller device 200 or an external device for use by a physician or practitioner. In some embodiments, the controller device 200 can write data onto the memory device 318. Recording this data on the memory device 318 within the disposable pump device can be useful, particularly when a user might detach and reattach a pump device 100 multiple times from the controller device 200 before discarding the pump device 100 when the fluid cartridge 120 is empty.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration while not fully surrounding the pump housing 110. Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable (as described below in connection with FIGS. 6-8). Moreover, at least one of the pump device 100 or the controller device 200 can include a release member that facilitates an easy-to-use detachment and replacement process.

Referring again to FIGS. 1-3, the pump system 10 can be a medical infusion pump system that is configured to controllably dispense a medicine from the cartridge 120. As such, the fluid cartridge 120 can contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, as shown in FIG. 1, the pump housing structure 110 can include one or more retainer wings 119 that at least partially extend into the cavity 116 to engage a portion of the medicine cartridge 120 when the medicine cartridge 120 is installed therein. Such a configuration may facilitate the "one-time-use" feature of the pump device 100 and ensure that an data stored on the memory device 318 is reflective of the one and only fluid cartridge 120. In some embodiments, the retainer wings 119 can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIGS. 1-3) of the pump device 100. The controller device 200 can also then be adapted to read data from (and in some embodiments write data to) the memory device 318 As described in more detail below, the pump device 100 can include a drive system that causes controlled dispensation of the medicine or other fluid from the cartridge 120. In some embodiments, the drive system incrementally advances a piston rod (not shown in FIGS. 1-3) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

Figure 16:
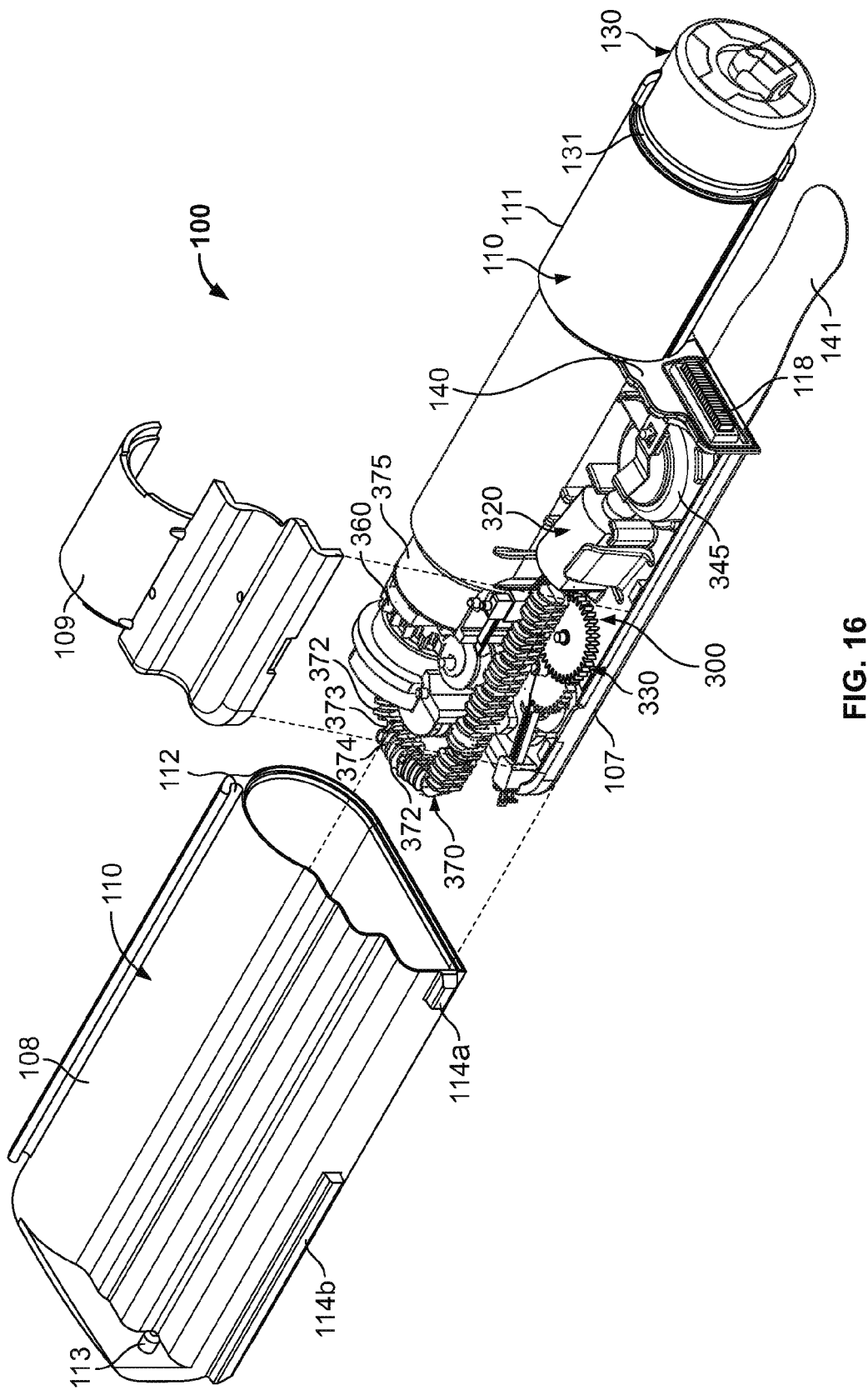
FIG. 16 is an exploded perspective view of a pump device for an infusion pump system, in accordance with some embodiments.

As shown in FIG. 1, the pump device 100 can include an electrical connector 118 (e.g., having conductive pads, pins, and the like) that are exposed to the controller device 200 and that mate with a complementary electrical connector (refer to connector 218 in FIG. 3) on the adjacent face of the controller device 200. The electrical connectors 118 and 218 provide the electrical communication between the control circuitry (refer, for example, to FIG. 16) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. In some embodiments, electrical connectors can permit for the transmission of data between the memory device 318 and the controller device 200. Furthermore, as described in more detail below, the infusion pump system 10 can include a gasket 140 that provides a seal that is resistant to migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 can include a user interface 220 that permits a user to monitor the operation of the pump device 100. In some embodiments, the user interface 220 can include a display device 222 and one or more user-selectable buttons (e.g., four buttons 224a, 224b, 224c, and 224d in this embodiment). The display device 222 can include an active area in which numerals, text, symbols, images, or a combination thereof can be displayed (refer, for example, to FIG. 2). For example, the display device 222 can be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. In some embodiments, an event log on the memory device 318 can record user interaction with the user interface (e.g., storing the date and time for each adjustment in settings or other programming of the controller device).

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

Figure 4:
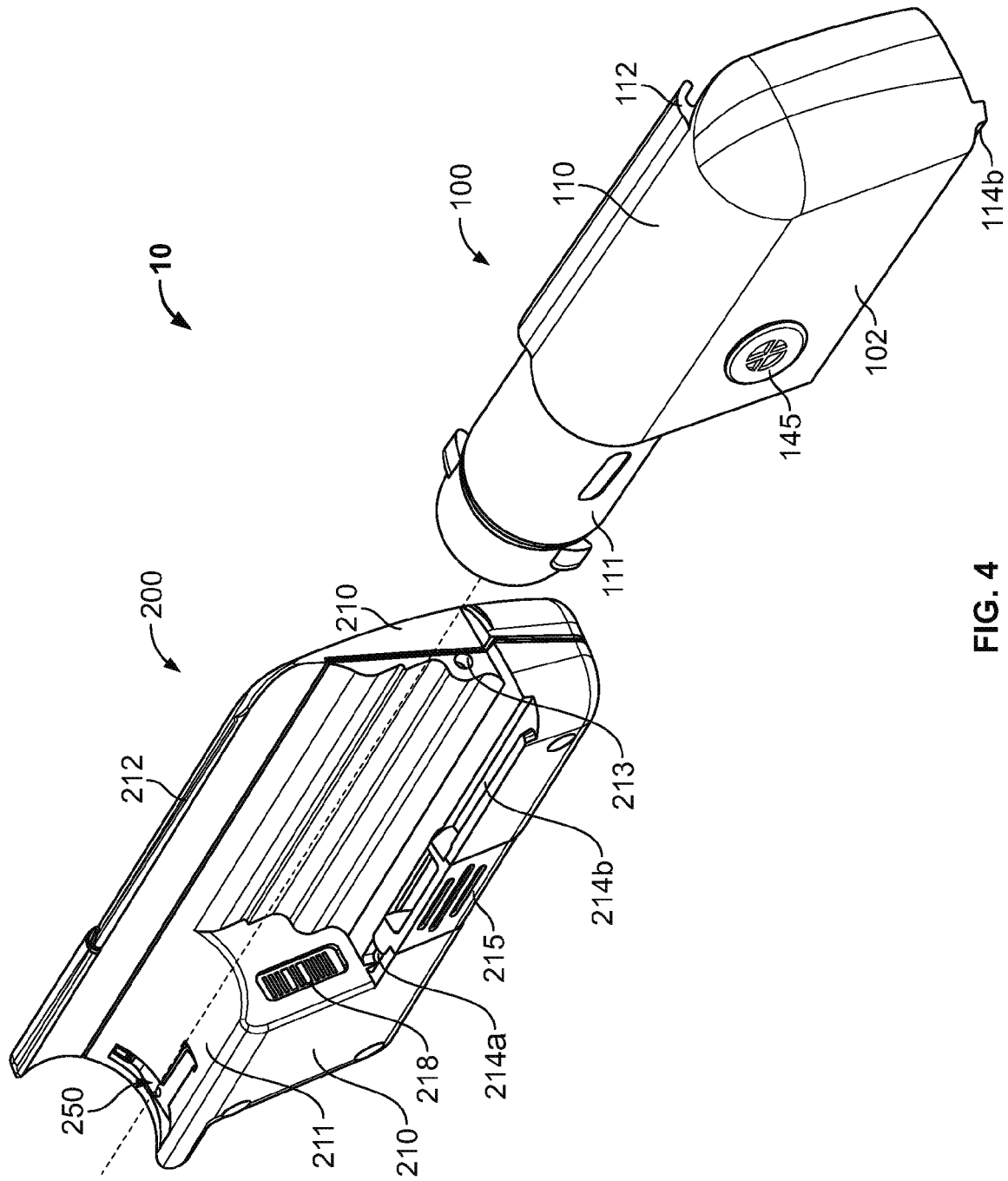
FIG. 4 is a perspective view of the infusion pump system of FIG. 1 in a detached state.
Figure 5:
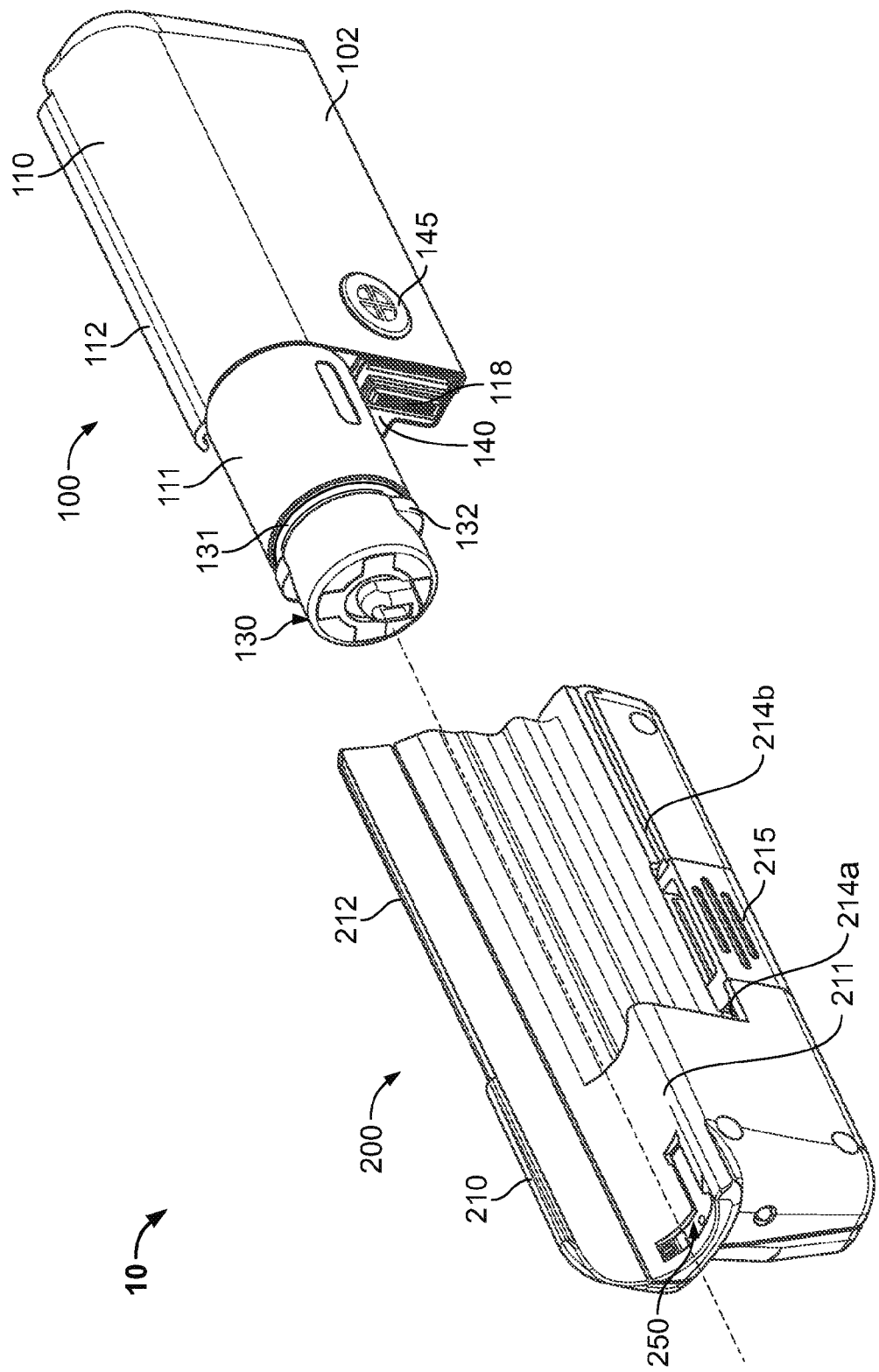
FIG. 5 is another perspective view of the infusion pump system on FIG. 4.

Referring now to FIGS. 4-5, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 13) toward the controller device 200 until the complementary features connect and secure the separate components in the side-by-side arrangement. In these circumstances, the pump device 100 and the controller device 200 can be separate components that fit together, but the overall size of the combined assembly can be reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user.

The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. Also, the pump housing 110 can include slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 can include a segmented rail 114a-b (FIG. 1) that mates with a guide channel 214a-b to direct the relative longitudinal motion between the pump device 100 and the controller device 200. As described in more detail below, the segmented rails 114a-b can interact with the release member 215 so as to releasably secure the pump device 100 into assembly with the controller device 200. In addition, the pump housing 110 can include an extension 113 (FIG. 1) that mates with a depression 213 (FIG. 5) in the controller housing 210 when the pump device 100 is fully attached to the controller device 200. It should be understood that, in other embodiments, other features or connector devices can be used to facilitate the side-by-side mounting arrangement. These other features or connector devices can include, for example, magnetic attachment device, mating tongues and grooves, mounting protrusions that friction fit into mating cavities, or the like. In some embodiments, the memory device 318 can include a number of compatibility codes corresponding to these features and the controller device 200 can detect those compatibility codes to ensure that the controller device 200 and the pump device 100 will properly mate. In some embodiments, a controller device 200 can indicate that a pump device 100 is not compatible if the pump device does not include a suitable set of compatibility codes for controller device 200.

Still referring to FIGS. 4-5, the pump device 100 and the controller device 200 can be attached in a manner that is resistant to migration of external contaminants (e.g., water, dirt, and the like) both into the pump housing structure 110 and the controller housing structure 210. For example, when the pump device 100 is advanced in the longitudinal direction toward the controller device 200 (as guided by the slider channel 112 and the segmented rails 114a-b), the electrical connector 118 (FIG. 5) of the pump device 100 is directed toward engagement with the mating connector 218 (FIG. 4) of the controller device 200. When the connectors 118 and 218 join together to form the electrical connection, the gasket 140 is compressed between the adjacent surfaces of the pump housing 110 and the controller housing 210. The gasket 140 thereby forms a water-resistant seal between the ambient environment and the mated connectors 118 and 218. Accordingly, in particular circumstances, the infusion pump system 10 can be assembled into a "water tight" configuration that protects sensitive internal components from water migration in the event that the user encounters water while wearing the pump system 10. In one example, the gasket 140 can resist migration of water to the electrical connectors 118 and 218 even when the system 10 is submerged underwater (e.g., in a pool, in a bath, or the like) for an extended period of time, such as at least 10 minutes, at least 30 minutes, at least one hour, at least two hours, and preferably at least four hours.

In addition, other paths for migration of external contaminants into the assembled pump system 10 can be sealed. For example, the infusion pump system 10 can include one or more seals that are arranged to hinder migration of external contaminants between the cap device 130 and the pump housing 110 into the cavity 116 of the pump device 100. In some embodiments, the seal 131 arranged between the cap device 130 and the barrel 111 can provide an effective water-resistant seal against water migration into the cavity. As such, the medicine cartridge 120 and pump drive system (not shown in FIGS. 4-5) can be protected during operation.

Figure 17:
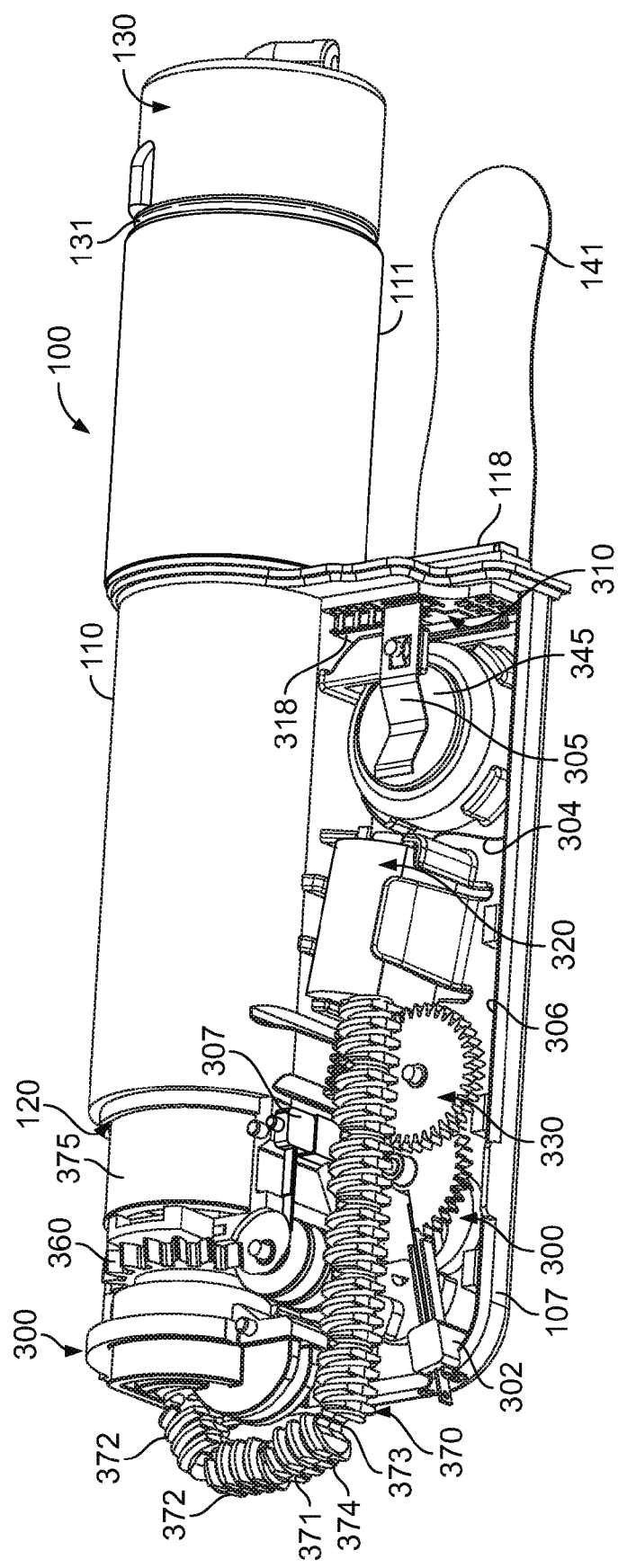
FIG. 17 is a perspective view of a portion of the pump device of FIG. 16.

Still referring to FIGS. 4-5, some embodiments of the infusion pump system 10 may employ a power source arranged in pump device 100 or the controller device 200 that draws upon surrounding air for optimum operation. Because the controller device 200 and the pump device 100 may be sealed to resist water migration during normal usage, a water-resistant vent instrument 145 can be used to provide the air to the power source without permitting migration of water therethrough. For example, the pump device 100 can contain a first power source 345 in the form of a zinc-air cell battery (refer to FIGS. 17 and 18), which draws upon the surrounding air during operation. When the pump device 100 is in use, the pump housing 110 can be sealed to protect the internal drive system and medicine cartridge from water migration. As such, the pump housing 110 can include a water-resistant vent instrument 145 disposed proximate to the first power source 345 (e.g., a zinc-air cell battery) so that some air may pass through the vent 145 and toward the first power source 345. The water-resistant vent instrument 145 can include one or more layers of a material that is permeable to air and resistant to passage of liquids such as water. For example, the water-resistant vent instrument 145 can include one or more layers of a GORE-TEX material to resist the migration of water into the pump device while permitting the passage of air toward the battery.

Accordingly, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 6:
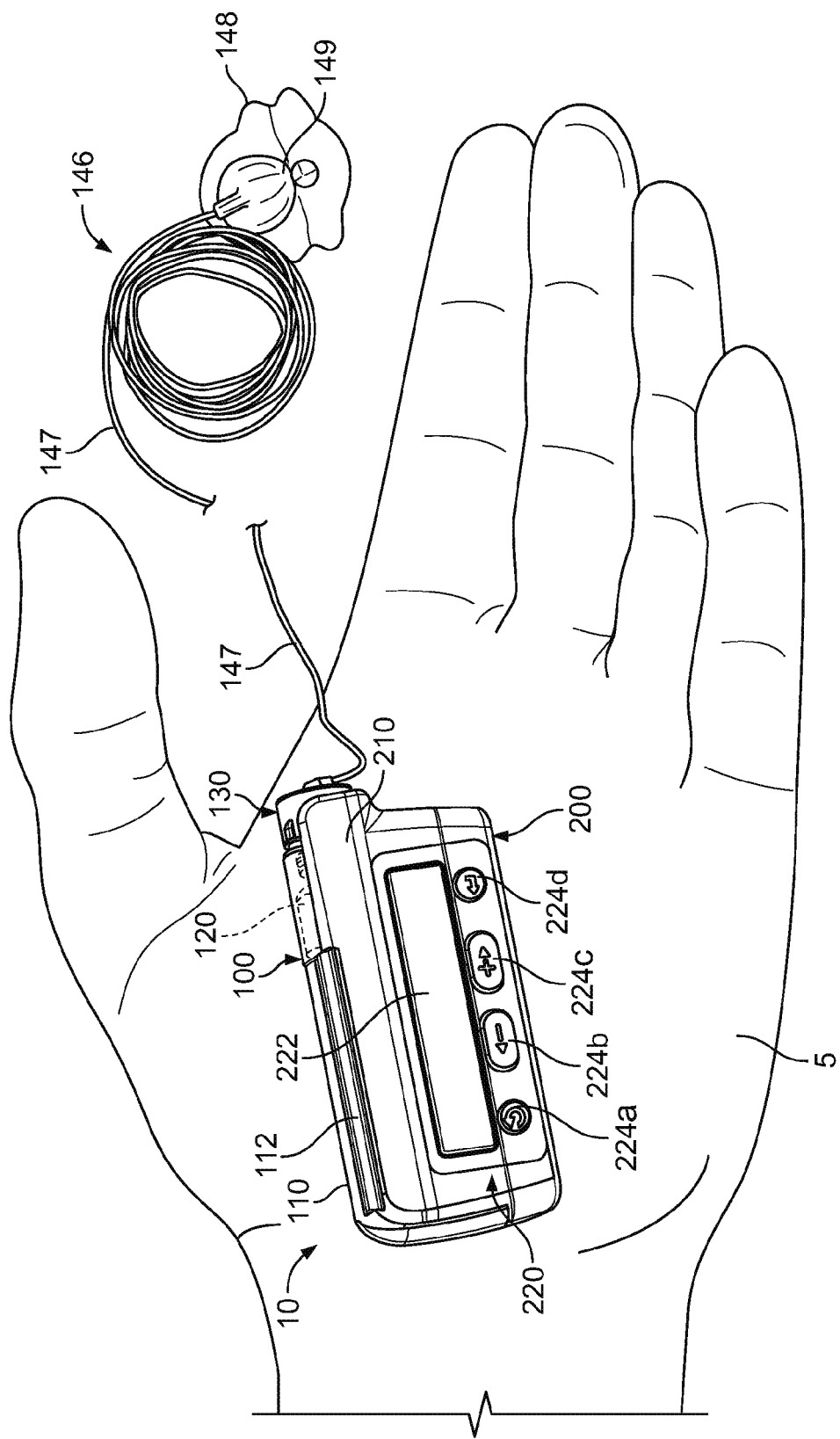
FIG. 6 is a perspective view of an infusion pump system, in accordance with some embodiments.
Figure 7:
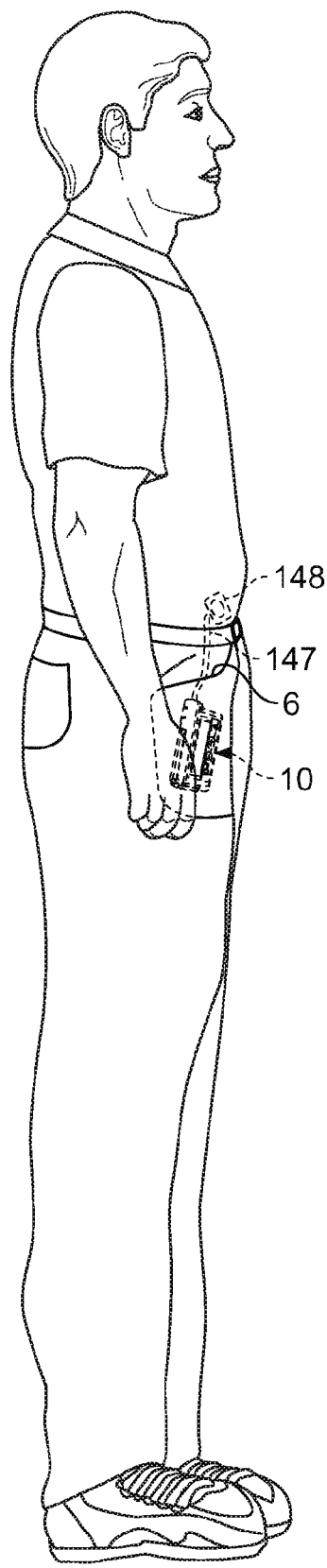
FIG. 7 is a perspective view of the infusion pump system of FIG. 5 worn on clothing of a user.
Figure 8:
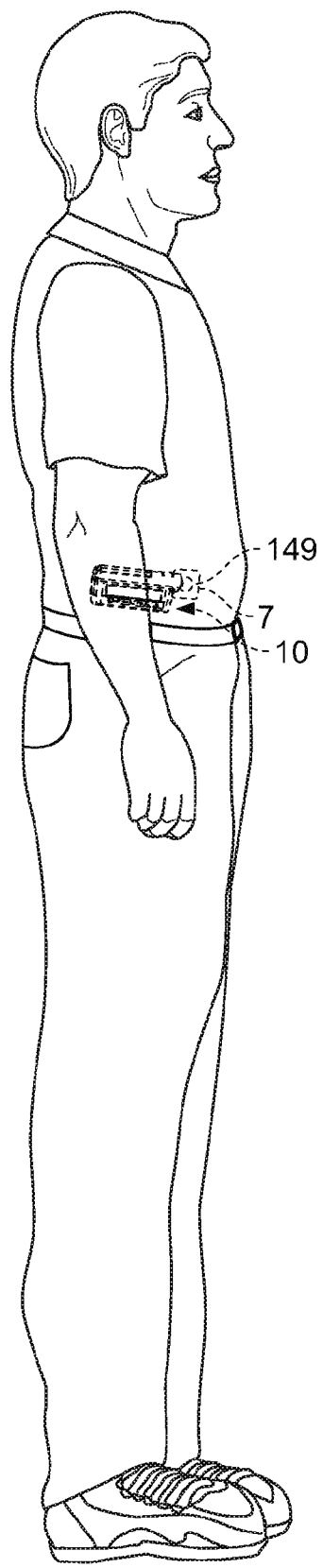
FIG. 8 is a perspective view of an infusion pump system worn on skin of a user, in accordance with particular embodiments.
Figure 9:
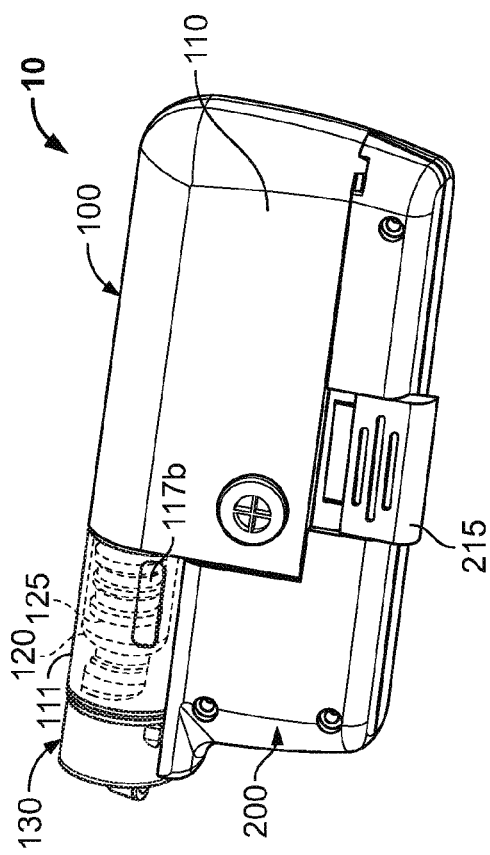
Figure 10:
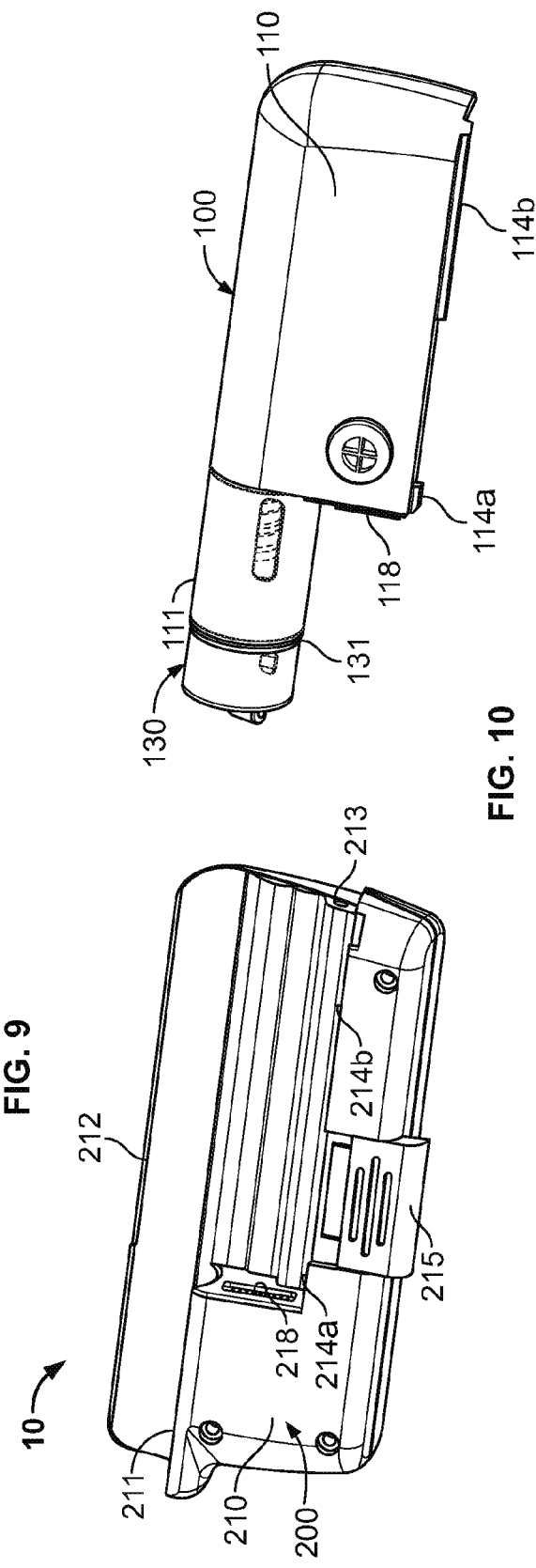

Referring to FIGS. 6-8, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. As described below in connection with FIGS. 17-18, the drive system of the pump device 100 can be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in some embodiments). In addition, the pump housing structure 110 can have an overall height of about 2 cm to about 4 cm (about 3.1 cm or less in some embodiments) and an overall thickness of about 8 mm to about 20 mm (about 17.5 mm or less in one embodiment).

The pump system 10 is shown in FIG. 6 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin) The infusion set 146 can include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

Referring to FIG. 7, in some embodiments, the infusion pump system 10 can be pocket-sized so that the pump device 100 and controller device 200 can be worn in the user's pocket 6 or in another portion of the user's clothing. In some circumstances, the user may desire to wear the pump system 10 in a more discrete manner. Accordingly, the user can pass the tube 147 from the pocket 6, under the user's clothing, and to the infusion site where the adhesive patch 148 can be positioned. As such, the pump system 10 can be used to delivery medicine to the tissues or vasculature of the user in a portable, concealable, and discrete manner.

Referring to FIG. 8, in some embodiments, the infusion pump system 10 can be configured to adhere to the user's skin 7 directly at the location in which the skin is penetrated for medicine infusion. For example, a rear surface 102 (FIG. 3) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin 7) so as to view and interact with the user interface 220.

Referring now to FIGS. 9-14, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics) while disposing of the relatively low-cost pump device 100 after each use. Such a pump system 10 can provide enhanced user safety as a new pump device 100' (and drive system therein) is employed with each new fluid cartridge 120. Although the pump devices 100 may be disposable, a user can disconnect and reconnect a pump devices 100 multiple times before discarding the pump devices 100 when the medicine cartridges 120 are empty.

Referring to FIGS. 11-12, the same controller device 200 can be reused with a new pump device 100' having a new medicine cartridge 120' retained therein, and the previously used pump device 100 can be discarded with the exhausted medicine cartridge 120. The new pump device 100' (FIG. 11) can have a similar appearance, form factor, and operation as the previously used pump device 100, and thus the new pump device 100' can be readily attached to the controller device 200 for controlled dispensation of medicine from the new medicine cartridge 120'. In some embodiments, however, additional pump devices can be used having different appearances, different form factors, and/or different operations. For example, in some embodiments, a user can use the reusable controller with pump devices 100 including different medications. In some embodiments, the user can prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 11, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the infusion set patch to the user's skin. As shown in FIG. 11, the new medicine cartridge 120' may be filled with medicine such that the plunger 125 is not viewable through the barrel 111.

Referring to FIGS. 13-14, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. The new pump device 100' can include the removable tab 141 to seal the battery in the unused pump device 100' and thereby maintain the battery in a storage mode (refer, for example, to FIG. 12 in which the removable tab 141 is arranged to cover an internal face of the vent 115). As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 can permit users to readily join the pump device 100' and the controller device 200 without compound or otherwise difficult hand movements—a feature that can be beneficial to child users or to elderly users.

Figure 15:
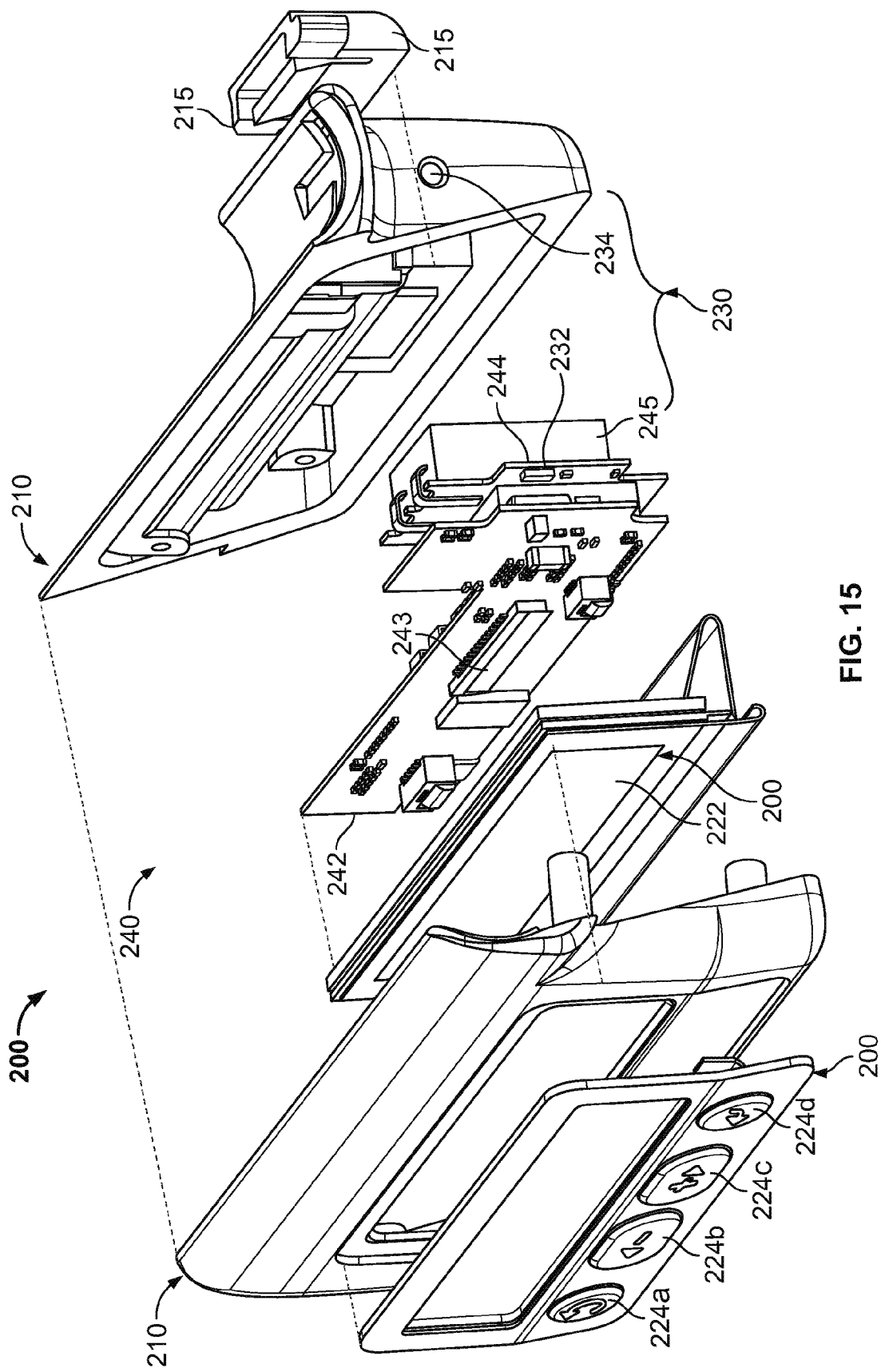

Referring now to FIG. 15, the controller device 200 (shown in an exploded view) houses a number of components that can be reused with a series of successive pump devices 100. In particular, the controller device 200 can include control circuitry 240 arranged in the controller housing 210 configured to communicate control signals to the drive system of the pump device 100. In some embodiments, the control circuitry 240 can include a main processor board 242 in communication with a power supply board 244. The control circuitry 240 can include at least one processor 243 that coordinates the electrical communication to and/or from the controller device 200 (e.g., communication between the controller device 200 and the pump device 100). The processor 243 can be arranged on the main processor board 242 along with a number of other electrical components, such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable, i.e., the user may provide one or more instructions to adjust a number of settings for the operation of the infusion pump system 10. Such settings may be stored in the memory devices arranged in the control circuitry 240. Furthermore, the control circuitry 240 can include one or more dedicated memory devices storing executable software instructions for the processor 243. The control circuitry 240 can include other components, such as sensors, that are electrically connected to the main processor board 242. For example, at least a portion of the occlusion sensor 250 (not shown in FIG. 15) can be electrically connected to the main processor board 242 via a flexible circuit substrate and/or one or more wires.

Still referring to FIG. 15, the user interface 220 of the controller device 200 can include input components and/or output components, that are electrically connected to the control circuitry 240. For example, the user interface 220 can include a display device 222 having an active area that outputs information to a user and four buttons 224a-d that receive input from the user. Here, the display device 222 can be used to communicate a number of settings or menu options for the infusion pump system 10. In some embodiments, the control circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). As previously described, the controller circuit 240 can be programmable to cause the controller circuit 240 to change any one of a number of settings for the infusion pump system 100.

Some embodiments of the control circuitry 240 can include a cable connector (e.g., a USB connection port or another data cable port) that is accessible on an external portion of the controller housing 210. As such, a cable can be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable can also provide recharging power.

Figure 18:
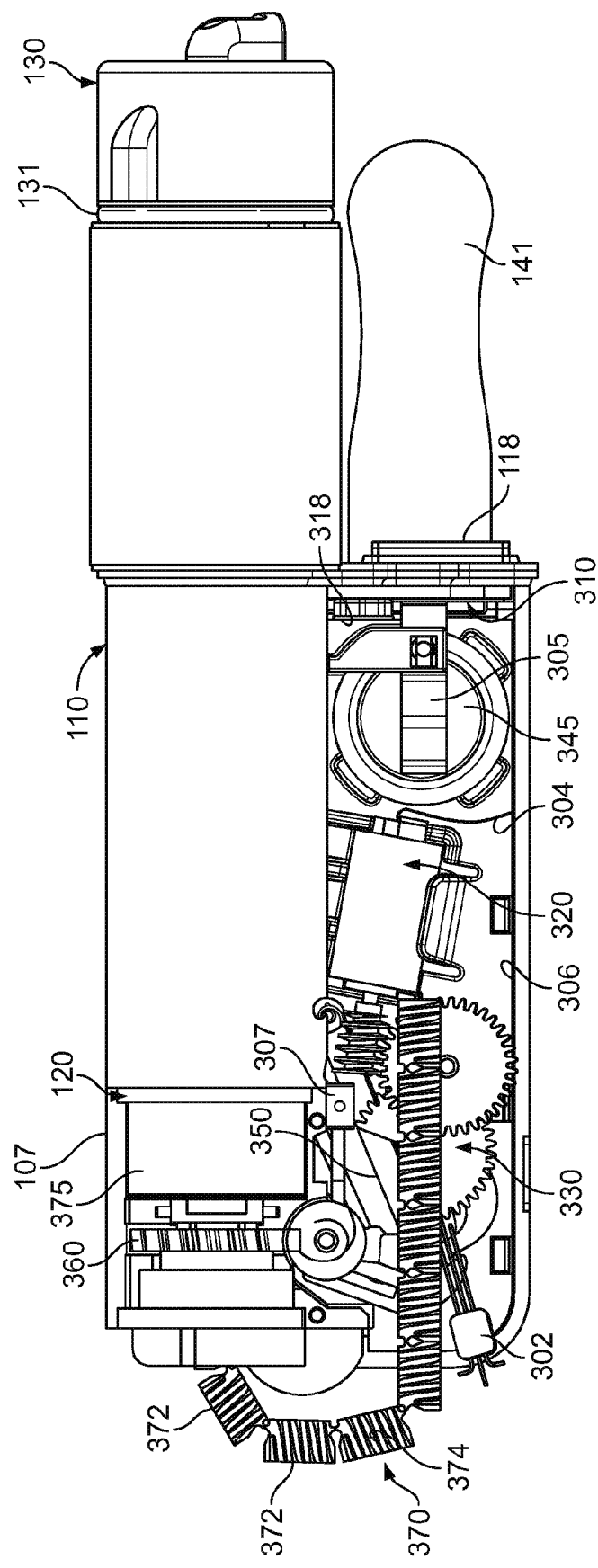
FIG. 18 is a top view of a portion of the pump device of FIG. 16.

In some embodiments, the pump device 100 can include a first power source 345 (refer to FIGS. 16-18) capable of transmitting electrical energy to the controller device 200 when the pump device 100 is attached to the controller device 200. Such energy transmission is described in more detail below. In some embodiments, the first power source 345 can be maintained in a storage mode and then switched to an activation mode when the pump device 100 is used to dispense medicine. The storage mode can provide a long shelf life of storage for the first power source 345. For example, when in storage mode, the first power source can retain a substantial portion of its charge for a period of more than six months, more than one year, or more than two years. As shown in FIGS. 12, 14, and 18, the first power source 345 can be equipped with a removable tab 141 that seals the first power source 345 to maintain it in the storage mode. Thus, when the pump device 100 is prepared for usage, the removable tab 141 can be pulled away from the pump housing 110, which switches the first power source into the activation mode. When the first power source 345 is switched to the activation mode, the first power source 345 can dispense electrical energy for a usage period in which the pump device is used. For example, in some embodiments, the first power source 345 can provide electrical energy to other components (e.g., the second power source 245) over a usage period of about one week to about one month (e.g., about two weeks).

The first power source 345 can include a disposable and/or non-rechargeable battery (e.g., a zinc-air cell). The first power source 345 can have a large volumetric energy density compared to the second power source 245. For example, the first power source 345 can be a zinc-air cell battery that has a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery can have a long storage life, as described above. One exemplary zinc-air cell battery is available from Duracell Corporation of Bethel, Conn., which can provide a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA•h (about 650 mA•h in one embodiment).

Referring again to FIG. 15, the control circuitry 240 of the controller device 200 can include a second power source 245, which can be coupled to the power supply board 244 of the control circuitry 240. The second power source 245 can be a rechargeable energy source (e.g., a lithium polymer battery). The second power source 245 can include a high current-output battery that is capable of discharging a brief current burst to power, for example, a drive system of the pump device 100 and can be capable of accepting and storing electrical energy over time (e.g., "trickle charge"). For example, the second power source 245 can be charged with energy supplied from the first power source 345. The hard-wired transmission of electrical energy from the second power source 245 to the drive system 300 can occur through the previously described connectors 118 and 218 (FIGS. 6-7). The second power source 245 can receive electrical energy from a power source housed in the pump device 100 (e.g., the first power source 345), from a plug-in wall charger, from a cable connector (e.g., a USB connection port that is connected to the control circuitry 240), or from another charging device (e.g., a charging cradle).

The second power source 245 can include a high current-output device that is contained inside the controller housing 210. The second power source 245 can be charged over a period of time (e.g., by a first power source 345) and can intermittently deliver high-current bursts to the drive system 300 over brief moments of time. For example, the second power source 245 can include a lithium-polymer battery. The second power source 245 (e.g., lithium polymer battery) disposed in the controller device 200 can have an initial current output that is greater than that of the first power source 345 (e.g., zinc-air cell battery) disposed in the pump device 100, but the first power source 345 can have an energy density that is greater than the second power source 245 (e.g., the lithium polymer battery disposed in the controller device 200 can have a volumetric energy density of less than about 600 Wh/L). In addition, the second power source 245 (e.g., lithium-polymer battery) can be readily rechargeable, which can permit the first power source 345 disposed in the pump device 100 to provide electrical energy to the second power source 245 for purposes of recharging. One exemplary lithium-polymer battery can provide a initial current output of about greater than 80 mA (about 90 mA to about 110 mA, and about 100 mA in one embodiment) and a maximum potential voltage of about 4.0V to 4.4V (about 4.2 V in one embodiment). In other embodiments, it should be understood that the second power source 245 can include a capacitor device capable of being recharged over time and intermittently discharging a current burst to activate the drive system 300.

Additional embodiments of the power source 245 can include a combination of batteries and capacitors.

Accordingly, the infusion pump system 10 can have two power sources 345 and 245—one arranged in the disposable pump device 100 and another arranged in the reusable controller device 200—which can permit a user to continually operate the controller device 200 without having to recharge a battery via a plug-in wall charger or other cable. Because the controller device 200 can be reusable with a number of pump devices 100 (e.g., attach the new pump device 100' after the previous pump device 100 is expended and disposed), the second power source 245 in the controller device can be recharged over a period of time, each time when a new pump device 100 is connected thereto. Such a configuration can be advantageous in those embodiments where the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 18, the pump device 100 can include the drive system 300 that is controlled by the removable controller device 200 (FIGS. 1-5). Accordingly, the drive system 300 can accurately and incrementally dispense fluid from the pump device 100 in a controlled manner. The drive system 300 can include a flexible piston rod 370 that can be incrementally advanced toward the medicine cartridge 120 so as to dispense the medicine from the pump device 100. At least a portion of the drive system 300 can be mounted, to the pump housing 110. In some embodiments, the pump housing 110 can include a chassis 107, a shell portion 108, and a cover mount 109. The shell portion 108 can be used to cover at least a portion of the drive system 300. For example, the shell 108 can include an inner curved surface against which a curved section of a piston rod 370 rests. The cover mount 109 may be assembled to the chassis 107 of the pump housing 110 to secure some components of the drive system 300 in position between the cover mount 109 and the chassis 107. When the cover mount 109 is assembled into place, the "unused" or retracted portion of the piston rod 370 can rest in a channel defined in the top of the cover mount 109. The shell portion 108 can slide over the cover mount 109 and join with the chassis 107 to form the assembled pump housing 110.

Some embodiments of the drive system 300 can include a battery powered actuator (e.g., reversible motor 320 or the like) that resets a ratchet mechanism 330, a spring device (not shown) that provides the driving force to the ratchet mechanism 330, and a drive wheel 360 that is rotated by the ratchet mechanism 330 to advance the flexible piston rod 370 toward the medicine cartridge 120.

As shown in FIG. 18, the pump device 100 can include one or more motion detectors coupled with the drive system 300 to provide feedback regarding the operation of the drive system 300. For example, the pump device 100 can include a first motion detector 302 configured as a limit switch that detects when a portion of the ratchet mechanism has reached the limit of its travel and must thereafter stop movement or reverse direction. In another example, the pump device 100 can include a second motion detector 307 in the form of a mechanical error switch that indicates whether components of the drive system 300 completed the desired motion for each drive cycle.

Referring to FIG. 18, the pump device 100 can include a connector circuit 310 to facilitate the transfer of signals to and from the electrical connector 118. As previously described, the electrical connector 118 of the pump device 100 can mate with the connector 218 (FIG. 5) of the controller device 200 so that electrical communication can occur between the pump device 100 and the controller device 200. The connector circuit 310 can include a generally non-complex circuit 310 that does not include a processor or other relatively high-cost components. In some embodiments, the connector circuit 310 can operate as a passageway for the control signals (from the control circuitry 240 (FIG. 15) of the controller device 200) to transmit to the drive system 300 (e.g., to the actuator 320). For example, the reversible motor 320 may be connected to the connector circuit 310 via one or more wires 304. The connector circuit 310 can also operate as a passageway for the electrical power from the first battery 345 (FIG. 17) to pass to the controller device 200 for recharging of the second battery 245 (FIG. 15). For example, the first battery 345 can be connected to the connector circuit 310 via one or more power contacts 305. Furthermore, the connector circuit 310 can operate as a passageway for feedback signals (e.g., from the motion detectors 302 and 307) to transmit to the control circuitry 240 (FIG. 15) of the controller device 200. For example, the limit switch 302 can be connected to the connector circuit 310 via one or more wires 306 (the one or more wires connecting the mechanical error switch 307 to the connector circuit 310 are not shown in FIG. 18).

The connector circuit 310 in the pump device 100 can include a memory device 318 that can store data regarding the pump device 100, its operational history, and the user. The memory device 318 can include nonvolatile memory (e.g., a flash memory chip), a Serial EEPROM powered by the power source in the controller device 200, static RAM and a power source to allow the static RAM to retain the stored data, or a combination thereof. The memory device 318 can be configured to store data such as: a unique serial number designated for the pump device 100; a manufacturer identifier code; a lot number code; a manufacturing date stamp; a model number; compatibility codes used to ensure that the pump device 100, the controller device 200, and the fluid cartridge 120 can work together; an energy requirement profile for the drive system of the pump device; user profile information; an event log including time and date stamped records of pump activations, user input, and/or sensor input; data regarding the pump battery life (e.g., the power remaining in the first power source 345); a drive cycle counter; an estimation of pump motor run time; the type of medicine contained in the fluid cartridge 120; and an estimation of the medicine remaining in the fluid cartridge 120. The data stored on the memory device 318 can be received by the controller device 200 or an external device for use by a physician. In some embodiments, the controller device 200 can communicate with the memory device 318 so as to write data onto the memory device 318. In some embodiments, some data on the memory device 318 may be write protected as a safety precaution.

In some embodiments, the memory device 318 can include data representing an estimate of the amount of medicine remaining in the fluid cartridge 120. This data can be used by the controller device 200 to alert a user as to how much medicine is remaining in the pump device 100. The estimate can be determined by identifying the cartridge capacity when the pump device 100 is first attached to the controller device 200 and subtracting an amount corresponding to the dose whenever the pump actuates. In some embodiments, the controller device 200 may determine cartridge capacity by a machine-readable indicia, by an optical, electrical, or mechanical feature of the cartridge, or by user input or selection. In some embodiments, a manufacturer may identify a fluid cartridge 120 capacity and a dose volume for each pump actuation and record the fluid cartridge 120 capacity and the dose volume on the memory device. During the use of the pump device 100, the controller device 200 can subtract a dose volume from the fluid cartridge 120 capacity for each pump actuation and rewrite the new fluid cartridge 120 capacity to the memory device 318. Accordingly, the controller device 200 can determine the remaining fluid cartridge capacity for a pump device 100 that has been partially used, detached, and again attached to the same or even a different controller device 200.

In some embodiments, the memory device 318 can include data indicating the battery life of a battery in the pump device 100. As discussed above, the pump device 100 can include a first power source 345 (e.g., a zinc-air cell), which may be used to charge the second power source 245 in the controller device 200. The first power source 345 can be a non-rechargeable battery. In some embodiments, the memory device 318 can store an indication of whether the battery life of first power source 345 in the pump device 100 is in a depleted or non-depleted state. The controller device 200 can determine if the first power source 345 is in a depleted state by detecting a voltage output of the first power source 345. If the voltage output of the first power source 345 falls below a threshold voltage (e.g., 0.6 V), the controller device 200 can record an indication that the first power source 345 is depleted in the memory device 318. This can prevent the controller device 200 from attempting to charge the second power source 245 within the controller device 200 with a depleted first power source 345 when a pump device 100 with a depleted first power source 345 is reattached to a controller device 200. In some embodiments, the memory device 318 can include data estimating the amount of battery life remaining for the first power source 345. The controller device 200 can update this estimation by counting the number of recharge operations, calculating an amount of self discharge from a self-discharge rate for the first power source 345, which can also be recorded in the memory device 318, and a time and date stamp for the first use of the pump device, for when tab 141 was removed and/or a manufacturing date for the pump device.

In some embodiments, the memory device 318 can include data indicating a medicinal fluid type, an unique serial number, a manufacturer identifier code, a manufacturing lot code, a manufacturing date and/or time stamp, and a model number. This data may be useful quality control information that remains with the pump device 100 throughout its shelf-life and operational life. In some embodiments, this data may be write protected. If, for example, a manufacturing error is identified for a particular pump device 100, the unique serial number, the manufacturer identifier code, the manufacturing lot code, the manufacturing date stamp, and/or the model number can be used to promptly identify when and/or where the error occurred. A manufacturing date and/or time stamp can also allow the controller device 200 to identify expired medication. Furthermore, this information can also be used to allow the controller device 200 to determine if the pump device 100 is compatible with the controller device 200 or if the pump device 100 includes the correct medical fluid cartridge 120 for the user.

In some cases, a user may want to administer different medical fluids at different points in time with the same pump system 10. As an example, Symlin® (pramlintide acetate) can be administered prior to eating to slow gastric emptying. In some embodiments of the pump system 10, the user can enter in data (e.g., via the user interface 220) about a meal prior to eating. After receiving data about the meal, the pump system 10 can request that the user remove the existing pump device 100, containing insulin for example, and replace it with pump device 100 containing Symlin®. After checking certain data (e.g., that the new pump device 100 does contain Symlin®, that there is Symlin® remaining, that the Symlin® is not expired, and the like), the pump system 10 can cause a bolus of Symlin® to be administered to the user. Upon infusion of the Symlin®, the pump system 10 can request that the insulin containing pump device 100 be re-attached.

Referring to FIG. 19, in some embodiments, the memory device 318 can include data indicating an event log including time and date stamped records of pump activations, user input, and/or sensor input. An visual representation of an event log can be similar to that shown in FIG. 19. The event log can also record time and date stamps for when a pump device was first used with a controller device 200 and/or for each reattachment of the pump device 100 to the controller device 200. This data can allow for the reconstruction of events if there is a pump failure or other adverse event. This data can also be retrieved by a physician or counselor to help check compliance with recommended dosages, diet protocols, and/or exercise regimes. Moreover, the recorded data of a user's medical dosages and eating habits can enhance the ability of the user or a medical practitioner to perform retrospective analysis and correction of the medicine delivery profile.

In some embodiments, the memory device 318 can include compatibility codes that can be used to ensure that the pump device 100, the controller device 200, and the cartridge 120 can work together. For example, controller device 200 can be adapted such that only a physician can program which medications the user is allowed to receive and pump devices can include compatibility codes in the memory device 318 indicating whether the medication in the pump device is compatible with that controller's settings. Furthermore, some pump devices may require an updated or older controller (or that the controller includes include particular software) and the compatibility codes can indicate to a controller that that particular pump device should not be actuated by that controller.

Referring to FIG. 20, in some embodiments, the memory device 318 can include data indicative of user profile information. For instance, the memory device 318 in the disposable pump device 100 can serve as a backup data system for the user profile information that is originally stored in the controller device 200. Exemplary user profile data can include a user's identifying information (e.g., name and/or social security number), the types of medication that a user is allowed to take, the different menu options available to the user, a user's physical characteristics (e.g., height, weight, gender, and the like), a user's insulin sensitivity (e.g., the users blood glucose to insulin ratio), how a user's blood glucose level responds to eating (e.g., blood glucose to carbohydrate ratio), how a user's blood glucose level responds to increased activity levels (e.g., blood glucose to activity ratio), treatment data (e.g., basal insulin rates, schedules, and/or profile), and the like. For example, when a pump device 100 is used with a controller device 200 for the first time, the controller device 200 may transfer a user profile to the memory device 318.

In some circumstances, the controller device 200 can initially interrogate the memory 318 to determine if a pump device 100 already stores user profile data (e.g., stored as backup data when the pump device 100 was previously attached to another controller device 200). If a pump device 100 is detached and reattached to the same controller device 200, the controller device 200 can verify that the pump device 100 is being for used the correct user by comparing the user profile data in the pump memory 318 to the user profile data stored in the controller device 200. Furthermore, if the user has two controller devices 200, the controller devices 200 should have the same user profile, thereby allowing the user to change controller devices 200.

Another feature of recording user profile data on the memory device 318 of the pump device 100 is that the memory device 318 can serve as a backup of the user profile in the case that the controller device 200 becomes inoperable or in the case that the user misplaces the controller device 200. In some embodiments, the controller device 200 can be configured such that only a physician can set some of the user profile information (e.g., the types of medications allowed and/or the menu options available to the user). This operation may facilitate that a user does not misuse the medication, that the user knows how to control her blood glucose level (e.g., as a user becomes more knowledgeable about her condition, how to control her condition, and how the infusion pump system operates, a physician or practitioner can allow the user access to more advanced features of the infusion pump system), and verify that the controller device 200 does not dispense the wrong medication in the case where the user obtained a pump device 100 containing the wrong medication. The user profile information stored on the memory device 318 of a pump device 100 can allow a user to more quickly make a clone of the controller device 200, without the need for access to the original controller device 200 and without the need to seek out her physician to program a new controller device 200. Furthermore, some of the information stored in the user profile can be information determined by the controller device 200 during use with the user, as opposed to information programmed into the controller by either the user or a physician or practitioner.

A new controller device 200, when first attached to a pump device 100 having a user profile recorded from an old controller device 200, can receive the user profile information from the memory 318 of the pump device 100 and allow the user to make a clone controller quickly and without the help of a physician or practitioner. In some embodiments, the user can review the user profile and accept or reject some portions of the profile (e.g., if the user's weight has changed). In some embodiments, some portions of the profile may be reviewed but not altered by the user without the intervention of a physician or practitioner (e.g., the types of medication allowed for the user or the menu options available to the user). In some embodiments, data regarding the menu options available to the user can be stored as user interface flags, which can be set at various levels (e.g., basic, intermediate, or advanced) or can specifically indicate which menu options are available to the user. In some embodiments, the controller device 200 may be configured to receive a user profile from the pump memory 318 only once. For example, the controller device 200 that has been previously programmed with user profile information from the pump memory 318 may thereafter ignore the user profile data when the pump device 100 is attached or can confirm that the user profile data matches the data previously stored in the controller device 200. In some embodiments, a new controller device 200 can require the user to input data to confirm that the person in possession of the pump device 100 and the new controller device 200 is the person associated with the user profile. For example, the new controller device 200 can request that a user input a security code or a portion of the user's social security number. If the user does not input information that matches information recorded in the user profile, the new controller device 200 can decline to be programmed by the user profile stored in the memory device 318 of the pump device 100. In some embodiments, the new controller device 200 can determine whether to store the user profile information on the memory device 318 of the pump device 100 based on a time and date stamp of when the user profile was uploaded. For example, an extended time period (e.g., about 6 months to about 12 months) from when the user profile was recorded on the memory device 318 can indicate that the user profile might be inaccurate.

In some embodiments, not shown, an individually removable memory device can be used to produce a user profile backup. For example, a flash memory device having a USB connection can be attached to the controller device 200 to receive the user profile information. The backup copy of the user profile information could then be used to program a second controller device 200 if the first is damaged or misplaced.

A date and time stamp of when the pump device 100 is first used can also ensure that the medicine in the pump device is not expired. For example, this time and data stamp for when the pump device 100 was first used can be associated with when the user profile data was first transferred to the memory device 318. This could identify the pump device to not only the first controller device 200 but also to additional controller clones.

Furthermore, the data storage processes described herein can be implemented on pump systems in which the controller device is not removable from the pump device. For example, in some embodiments, the infusion system can include a pump unit that houses the drive system, the control circuitry, the energy source, and the first memory device (without a removable controller housing). In such circumstances, an individually removable memory device can be used to produce a user profile backup. For example, a flash memory device having a USB connection can be attached to the pump unit to receive the user profile information from the control circuitry housed therein. The backup copy of the user profile information could then be used to program a second pump unit if the first is damaged or misplaced.

Figure 21:
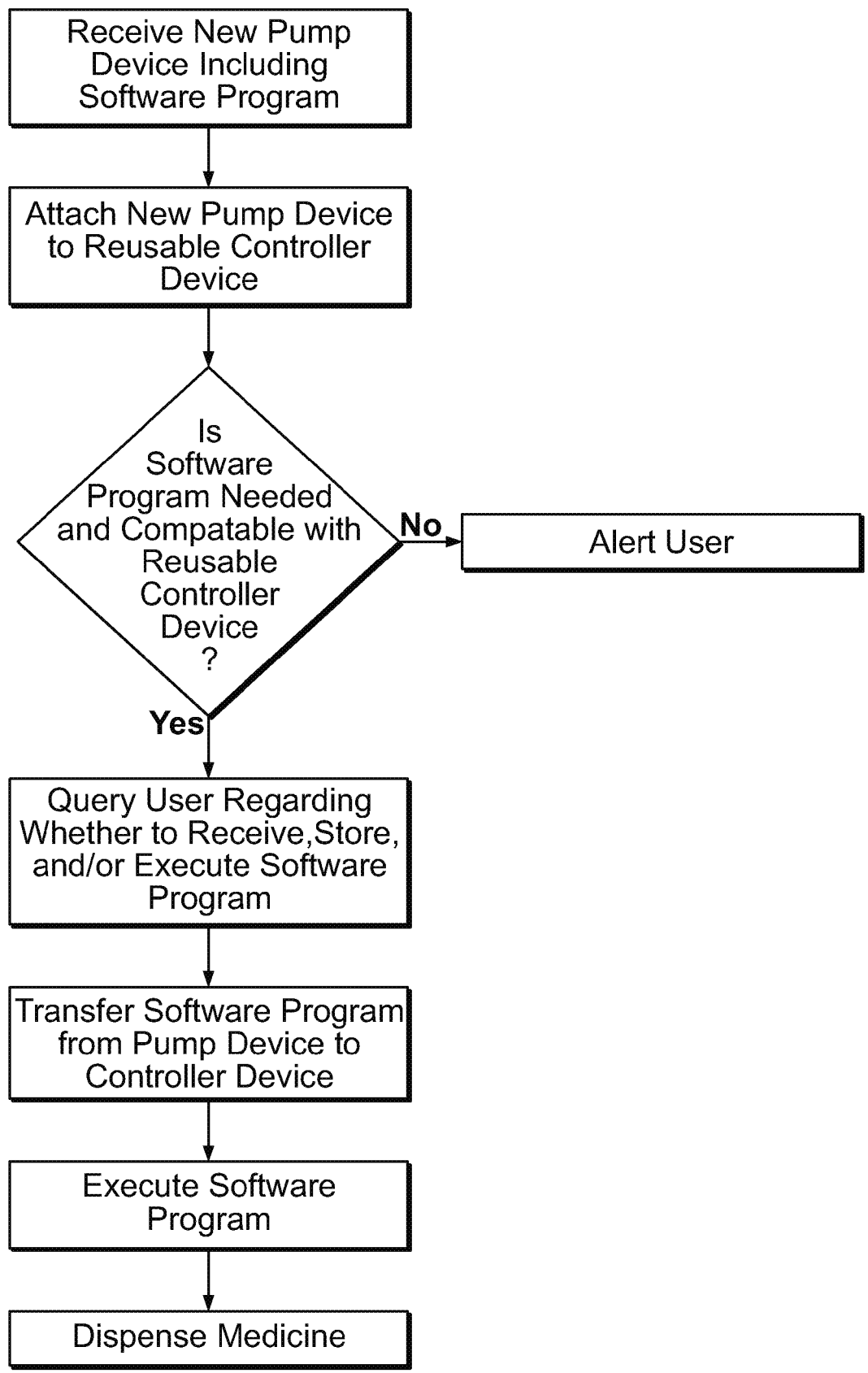
FIG. 21 is a flow diagram of how a user can update a software program in the controller device.

Referring now to FIG. 21, in some embodiments, the memory device 318 can include a software program including machine executable instructions. The software program can be a software update (e.g., a patch) for the controller operation software stored in a memory device of the control circuitry 240 or an entirely new software program for use with the controller device 200. The software program stored in the memory device 318 can also include identifying information that would allow the controller to determine whether the controller device 200 should receive, store, and/or execute the software update (e.g., whether the controller device 200 already included the software update or whether the software update is compatible with the particular model of the controller device 200). In some embodiments, the controller device 200 can query the user regarding whether to receive, store, and/or execute the software program. For example, the process of receiving and updating the software can require excessive time or add features that the user may not desire. In some embodiments, the software program stored in the memory device 318 can include an indication of whether the user should be queried regarding whether to receive, store, and/or execute the software program. Alternatively, the software program stored in the memory device 318 can be automatically transmitted to the controller device 200 and executed by the control circuitry 240 without any user interaction. In some embodiments, the software program can update selected portions of machine executable instructions stored in the memory devices of the control circuitry 240 according to the software program transferred from the memory device 318 of the pump device 100.

In some embodiments, a manufacturer can include the software program (e.g., a software update or patch) on the memory device 318 for use with the controller device 200 as a way of distributing a software update for the controller device 200. The controller device 200 can then perform the update either by overwriting its main program entirely with the new code, or by patching selected portions or subroutines according to a list in the software program of the pump memory 318. For example, as shown in FIG. 21, a user can receive a new pump device 100 including the software program and then releasably attach the new pump device 100 to their controller device 200. The controller device 200 can communicate with the memory device 318 in the pump device 100 to thereafter determine whether the software update is needed and/or compatible and, in some embodiments, query the user regarding whether to receive, store, and/or execute the software program. The controller device 200 can then transfer the software program to memory of the control circuitry 240 and execute the software program now stored in the controller memory. In some embodiments, the execution of the software program can reprogram the controller device 200. In other embodiments, the software program can be executed to perform various controller functions (e.g., to issue new user alerts, queries, or to allow for additional user input). After the controller device 200 has been updated with the new software program, the controller device 200 can then be used to perform medicine dispensing operations. In other embodiments, a physician or other medical practitioner can allow a user to update the software program on the controller device 200 by uploading a software program to the memory device 318 in the pump device 100.

As previously described, the memory device 318 can include pump motor run time or pump activation cycle count. This data can be used to limit use of the pump device 100 when it has been determined that the pump device 100 has exceeded its usable life. The drive cycle counter can also be useful for maintaining an accurate estimate of the volume of medicine that remains in the medicine cartridge 120. For example, the number of drive cycles that are required to incrementally advance the plunger 125 and thereby dispense a full medicine cartridge 120 may be a predetermined value (e.g., in some embodiments, 6,300 drive cycles result in full dispensation of a new medicine cartridge). Accordingly, the drive cycle counter stored in the memory device 318 can keep track of the number of drive cycles that have occurred through the operational life of the pump device 100. Each time the motor 320 completes a new drive cycle and incrementally advances the piston rod 370 to dispense some medicine, the controller device 200 can store an updated value for the drive cycle counter stored in the memory device 318. When the updated value stored in drive cycle counter stored in the memory device 318 approaches the predetermined value, the controller device 200 can alert the user that the medicine cartridge is approaching exhaustion. Furthermore, because the memory device 318 is arranged in the pump device 100, the drive cycle counter stored in the memory device 318 remains local to the pump device 100. If the pump device 100 is temporarily disconnected from the controller device 200 and then reconnected (or reconnected to a different controller device 200), the controller device 200 can retrieve the value for the drive cycle counter stored in the memory device 318 and promptly ascertain how much medicine remains in the medicine cartridge 120.

In some embodiments, the memory device 318 can include a microcontroller. For example, the memory device 318 can include an EEPROM device integrated on-chip, and the microcontroller can be capable of running a communication protocol between the controller device 200 and the pump device 100. The microcontroller can, in some embodiments, multiplex signals from limit switches or other sensors required to operate the pump mechanics and/or confirm a series of operations directed by the controller. In some embodiments, the microcontroller can update the data stored on the memory device 318 regarding, for example, the number of drive cycles. By having the microprocessor update the data on the memory device 318, the number of pin connectors between the pump device 100 and the controller device 200 can be reduced.

Figure 22:
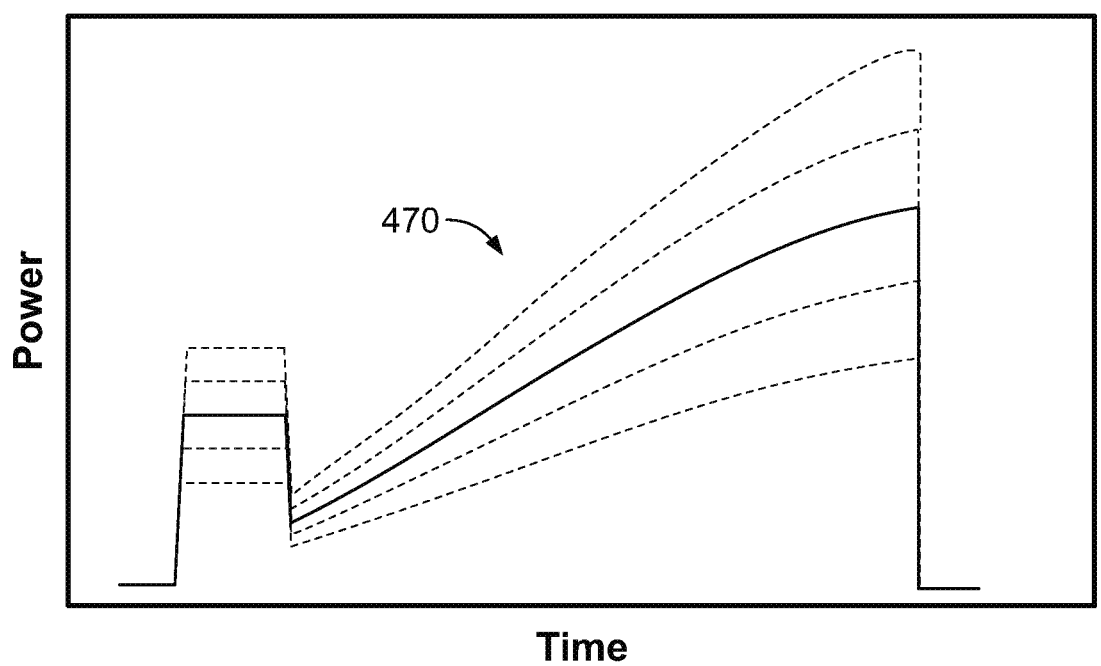
FIG. 22 is a graphs depicting a variety of drive system energy requirement profiles.

Referring to FIG. 22, in some embodiments, the memory device 318 can include a energy requirement profile for the drive system of the pump device 100. In some embodiments, the infusion pump system 10 can include a pulse width modulation (PWM) system for controlling the power delivery to the drive system 300. The drive system 300 can define an energy requirement profile to perform a medicine dispensing operation (e.g., a torque profile) and this energy requirement profile can be stored on the memory device 318. For example, an energy requirement profile can be similar to that shown in FIG. 22. As shown in FIG. 22, the PWM system can supply a pattern pulses of energy (voltage) 410, of varying widths or with varying timing, to provide a delivered energy profile 400 that correlates to the energy requirement profile 470 (e.g., a torque profile) of the drive system 300. Different drive systems for different pump device, however, can have different energy requirement profiles 470 (e.g., the different dashed lined profiles). Accordingly, by supplying an energy requirement profile 470 in the memory device 318 in the pump device 100, the controller device 200 can readily determine the appropriate pattern of pulses of voltage to supply the drive system to provide the optimal amount of energy to the drive system of that particular pump device 100.

For example, the energy requirement profile can be developed to optimize a plurality of variables, such as power consumption, gear RPM, and the like and the PMW system can be configured to provide a pattern of voltage pulses correlated to the energy requirement profile from the second power source 245 (e.g., the lithium polymer battery) to the drive system. In some embodiments, the torque profile can be developed to maintain the motor 320 at a constant rate of rotation, in spite of changing torque demands on the motor 320 (e.g., from the drive system 300). Maintaining the motor 320 at a substantially constant rate of rotation can have the advantageous qualities of reducing power consumption, reducing vibration, and/or increasing the life of the motor 320.

In some embodiments, the controller device 200 can detect whether the drive system 300 completes the medicine dispensing operation and adjust the delivered energy profile to meet the energy requirement profile needed for the drive system. The controller device 200 can store the delivered energy profile as an adjusted energy requirement profile for that particular pump device 100. For example, an energy requirement profile for a pump device can be stored in the memory device 318 in the pump device. In cases where the controller device 200 adjusts the delivered energy profile to meet the energy requirement profile needed for the drive system, the controller device 200 can update the energy requirement profile stored on the memory device 318 for subsequent medicine dispensing operations.

Referring to FIG. 22, a drive system can have varying energy requirement profiles 410 (as shown in the dotted lines). This torque curve can represent the torque that is estimated to maintain a constant RPM of the motor 320 when rotating in a first rotational direction that advances the ratchet mechanism 330 to elongate the spring device 350. This torque curve 400 can be a sum of, for example, the torque curve associated with initial motor 320 startup, the torque curve associated with the no load torque of the motor 320, the torque curve associated with the torque required to elongate the spring device 350, and the torque curve associated with the mechanical advantage that is achieved due to the connection of the ratchet mechanism 330 to the gear system. While the torque curve 470 here is described as a sum of other torque curves, the torque curve 470 could be determined from empirical data, for example by testing one or more pump devices 100 to determine the actual torque at any given time in a pump cycle required to keep the rate of rotation of the motor 320 substantially constant. In some embodiments, the torque curve 470 determined from a sum of other torque curves could be recorded in the memory device 318 at the time of manufacture of the pump device 100. In some embodiments, a manufacturer can test the pump device 100 after manufacture to find the optimal torque curve 470 and record that on the memory device 318. In other embodiments, a controller device 200 could determine the optimal torque curve for a particular pump device 100 and record the torque curve on the memory device 318. In some embodiments, a tachometer can be used to determine an optimum PWM profile for a particular pump device. In embodiments having a brush DC motor, motor commutation can be used as a tachometer surrogate. With a brushless motor the commutation signals are already in digital form and these digital signals can be used as a tachometer signal by measuring their frequency and/or period. It may also be possible to use the actuation period of the drive (interval between limit switch actuations) to provide feedback to the PWM controller to optimize the profile. For example, a PWM profile that provides more power than necessary will result in a faster actuation time, while a PWM profile that fails to provide the optimal amount of power can result in a sluggish actuation or even fail to start the actuation process.

In some embodiments, the controller device 200 can detect a time period for the drive system to complete a medicine dispensing operation and adjust the delivered energy profile to meet the energy requirement profile needed for the drive system. For example, a PWM profile that provides more energy than required can result in a more rapid actuation of the pump device. If the controller device 200 detects that the drive system completed the medicine dispensing operation in less time than a predetermined actuation time, then the controller device 200 can downwardly adjust the delivered energy profile. If the actuation takes more time than a predetermined actuation time, the controller device 200 can upwardly adjust the delivered energy profile. For example, a controller device 200 can correct a torque curve 470 initially recorded in the memory device 318 using one of the torque curves 470 shown in FIG. 22 in dashed lines, by upwardly or downwardly adjusting the curve 470 to further optimize the actuation of the drive system 300. In some embodiments, the controller device 200 can store the delivered energy profile as an adjusted energy requirement profile for the pump. For example, an energy requirement profile for a pump device can be stored in the memory device 318 in the pump device. In cases where the controller device 200 adjusts the delivered energy profile to meet the energy requirement profile needed for the drive system, the controller device 200 can update the energy requirement profile stored on the memory device 318 for subsequent medicine dispensing operations. In some embodiments, the controller device 200 can also detect whether the actuation of the pump actually begins and upwardly adjust the delivered energy profile if the pump fails to start.

Figure 23:
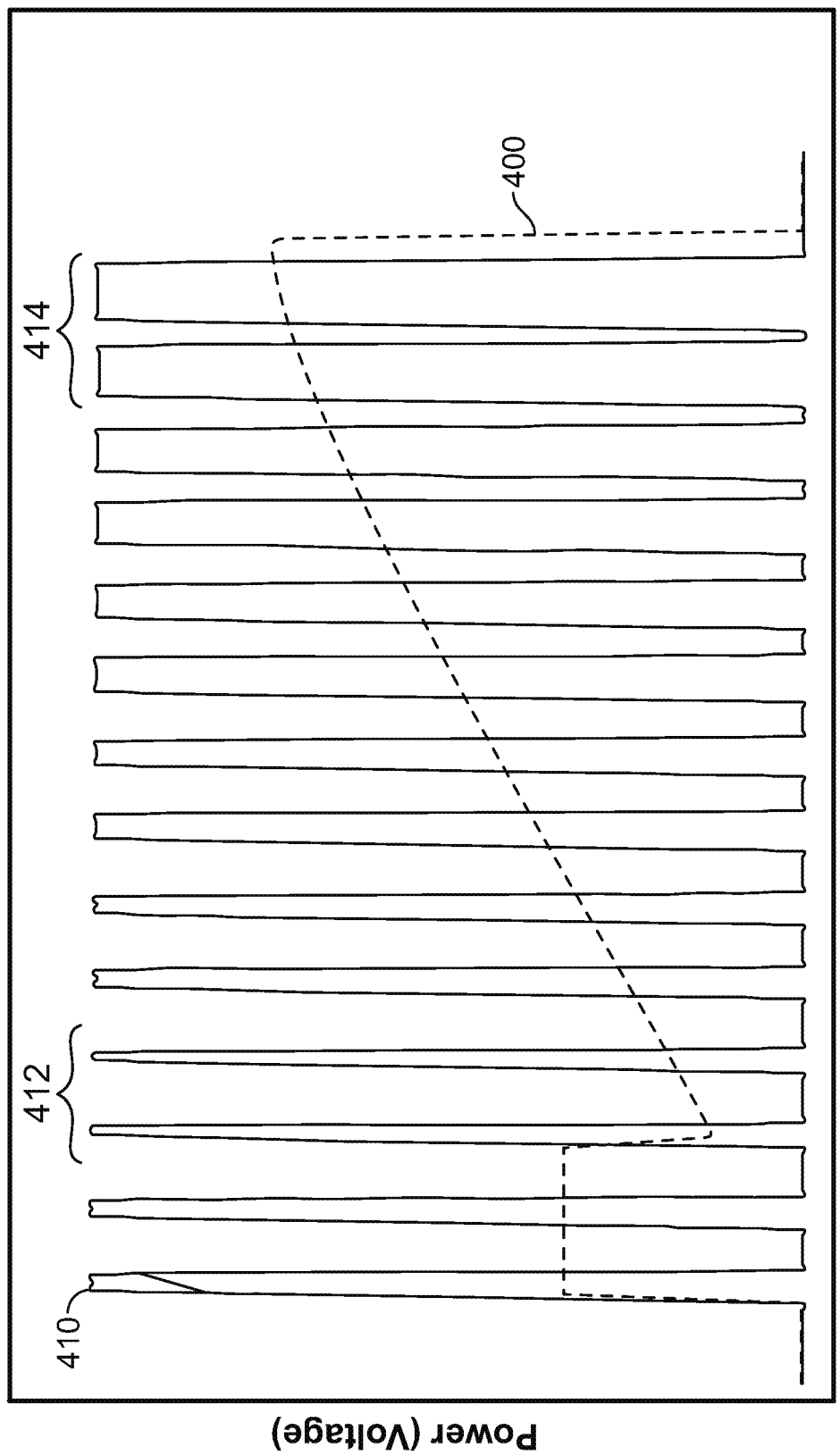
FIG. 23 is graphs depicting an example of a pattern of delivered voltage pulses and an energy profile created by that pattern of delivered voltage pulses.

Referring to FIG. 23, a PWM controller system can work by supplying intermittent, full-voltage, pulses of energy to supply a given amount of energy to a device (e.g., the motor 320) during a period of time. In some embodiments of the infusion pump system 10, the controller device 200 can supply a variable voltage to the motor 320 to achieve a predetermined torque curve (e.g., the continuous torque curve 470 shown in FIG. 21) using a digital-to-analog (D/A) converter and a power amplifier. In other embodiments, the system 10 can use a series of pulses, all at the full output voltage (e.g., a PWM system) to simulate a continuous torque curve (e.g., torque curve 400) without the need for a D/A converter or power amplifier and without the power loss associated with these components. One exemplary series of PWM pulses is depicted by a PWM torque curve 400 in FIG. 22. Referring to FIG. 23, the continuous torque curve 400 has been superimposed on the PWM pattern 410. When the torque demands on the motor 320 are low, the width of the delivered pulses is decreased (as in pulses 412). As the torque demands on the motor increase, the width of the delivered pulses is increased (as in pulses 414). Embodiments of the system 10 that employ a technique for limiting the torque supplied by the motor 320 have the advantage of controlling the RPM of the motor 320, thus conserving energy and reducing vibration associated with over-revving of the motor 320.

In some embodiments of the system 10, the voltage received by the drive system 300 from the second power source 245 can vary due to, for example, the charge remaining in the second power source 245. However, as the output voltage of the second power source 245 rises and falls, these pulse widths can be adjusted to supply the necessary torque. In one embodiment, a scalar multiple can be applied to the duration of the pulse width to correct for increased or decreased voltage. For example, if the sampled supply voltage to the motor 320 is 3.2 V, instead of the 4V rated output voltage, a scalar multiplier (e.g., 1.25) can be applied to the pulse width to correct for the change in voltage. In the preceding embodiments of the PWM system, the voltage of the pulses remained constant, while the width of the pulses were adjusted to maintain the motor 320 at a constant RPM. It should be clear to one skilled in the art that other embodiments of the pulse width modulation system could employ other methods. In one alternate example, the pulse widths could be kept constant, while the pauses in between the pulses could be increased or decreased to simulate a pre-determined torque curve. In additional embodiments, the RPM of the motor 320 could be monitored and the pulse widths could be adjusted based on the RPM of the motor 320. In some embodiments, the controller and/or the pump device 100 can store a series of tables in memory for converting between a detected voltage output and an adjustment to the pulse duration (pulse widths) and/or pulse frequency. For example, a detected voltage output of between 3.4 V and 3.5 V can result in the use of a particular table defining a particular PWM pattern for voltage outputs in that range or a particular scalar multiplier adjustment to another PWM pattern stored in memory. The use of tables for particular voltage outputs can reduce the number of computations needed to adjust the PWM pattern for changes in voltage output.

A number of embodiments have been described. Nevertheless, it will be understood that various modifications may be made without departing from the spirit and scope of this disclosure. Accordingly, other embodiments are within the scope of the following claims.

What is claimed is:

1. A wearable infusion pump system comprising:
   a pump device including a pump housing defining a space to receive a medicine source, the pump device including a drive system to dispense medicine from the pump device when the medicine source is received in the space, the pump device including a non-rechargeable battery positioned within the pump housing, the pump device including a memory device positioned within the pump housing storing data indicative of a charge level of the non-rechargeable battery positioned within the pump housing; and
   a controller device removably attachable to the pump housing of the pump device, the controller device housing control circuitry and at least one memory device that is different from the memory device positioned within the pump housing, wherein when the controller device is removably attached to the pump housing of the pump device, the controller device activates the drive system to dispense the medicine source and receives from the memory device positioned within the pump housing the data indicative of the charge level of the non-rechargeable battery, wherein the memory device positioned within the pump housing stores the data indicative of the charge level of the non-rechargeable battery positioned within the pump housing when the pump device is detached from the controller, and wherein the controller device is configured to query the memory device positioned within the pump housing and store the data indicative of the charge level of the non-rechargeable battery in response to attaching the pump device to the controller device.

2. The system of claim 1, wherein the controller device includes a user interface comprising a display device.

3. The system of claim 1, wherein the pump device includes at least one structure that hinders reuse of the pump device after the medicine source is exhausted such that the pump device is non-reusable and disposable.

4. The system of claim 1, wherein the data regarding the charge level of the non-rechargeable battery indicates whether the non-rechargeable battery is in a depleted or non-depleted state.

5. The system of claim 4, wherein the controller device includes a rechargeable energy source that is different from the non-rechargeable battery of the pump device.

6. The system of claim 1, wherein the controller device comprises a controller housing and first electrical contacts exposed along an exterior of the controller housing, wherein the pump device comprises second electrical contacts exposed along an exterior of the pump housing, and wherein when the controller device is removably attached to the pump device, the first electrical contacts and the second electrical contacts provide an electrical connection between the controller device and the pump device.

7. The system of claim 6, wherein the control circuitry is in electrical communication with the memory device housed in the pump device via the electrical connection when the controller device is removably attached to the pump device.

8. The system of claim 1, wherein: the pump device includes a cap device attachable to the pump housing structure such that a penetration member of the cap device extends into an interior of the space to penetrate a septum when the medicine source is received in the space; and the controller device includes a controller housing, a user interface display and user-selectable inputs for programming the controller device, and an energy storage source positioned within the controller housing.

9. The system of claim 8, wherein the pump device includes at least one structure that hinders reuse of the pump device after the medicine source is exhausted such that the pump device is non-reusable and disposable.

10. The system of claim 8, wherein the controller device comprises first electrical contacts exposed along an exterior of the controller housing, wherein the pump device comprises second electrical contacts exposed along an exterior of the pump housing, and wherein when the controller device is removably attached to the pump device, the first electrical contacts and the second electrical contacts provide an electrical connection between the controller device and the pump device.

11. The system of claim 10, wherein the control circuitry is in electrical communication with the memory device housed in the pump device via the electrical connection when the controller device is removably attached to the pump device.

12. The system of claim 8, wherein the control circuitry is in electrical communication with the memory device positioned in the pump housing so as to access the data of the memory device when the controller device is removably attached to the pump device.

13. The system of claim 12, wherein the data regarding the charge level of the non-rechargeable battery indicates whether the non-rechargeable battery is in a depleted or non-depleted state.

14. The system of claim 13, wherein the energy storage source of the controller device is a rechargeable energy source that is different from the non-rechargeable battery positioned in the pump housing.

15. The system of claim 14, when the data stored in the memory device regarding the charge level of the battery indicates that the battery is in the depleted state, the controller device ceases recharging of the rechargeable energy source positioned in the controller housing from the battery positioned in the pump housing.

16. A wearable infusion pump system comprising:
   a pump device including a pump housing defining a space to receive a medicine source, the pump device including a drive system to dispense medicine from the pump device when the medicine source is received in the space, the pump device including a battery positioned within the pump housing, the pump device including a memory device positioned within the pump housing storing data indicative of a charge level of the battery positioned within the pump housing; and
   a controller device removably attachable to the pump housing of the pump device, wherein when the controller device is removably attached to the pump housing of the pump device, the controller device activates the drive system to dispense the medicine source and receives from the memory device positioned within the pump housing the data indicative of the charge level of the battery;
   wherein the battery is a non-rechargeable battery;
   wherein the data regarding the charge level of the battery indicates whether the battery is in a depleted or non-depleted state;
   wherein the controller device includes a rechargeable energy source that is different from the battery of the pump device; and
   when the data stored in the memory device housed in the pump device regarding the charge level of the battery indicates that the battery is in the depleted state, the controller device ceases recharging of the rechargeable energy source housed within the controller device from the battery housed in the pump housing of the pump device.

17. The system of claim 16, wherein the controller device includes a user interface comprising a display device.

18. The system of claim 16, wherein the pump device includes at least one structure that hinders reuse of the pump device after the medicine source is exhausted such that the pump device is non-reusable and disposable.

19. The system of claim 16, wherein: the pump device includes a cap device attachable to the pump housing structure such that a penetration member of the cap device extends into an interior of the space to penetrate a septum when the medicine source is received in the space; and the controller device includes a controller housing, a user interface display and user-selectable inputs for programming the controller device, and an energy storage source positioned within the controller housing.

20. The system of claim 16, wherein the controller device comprises a controller housing and first electrical contacts exposed along an exterior of the controller housing, wherein the pump device comprises second electrical contacts exposed along an exterior of the pump housing, and wherein when the controller device is removably attached to the pump device, the first electrical contacts and the second electrical contacts provide an electrical connection between the controller device and the pump device.

21. The system of claim 20, wherein the controller device comprises control circuitry positioned in the controller housing, the control circuitry being in electrical communication with the memory device housed in the pump device via the electrical connection when the controller device is removably attached to the pump device.

* * * * *